(12) United States Patent
Goodman et al.

(10) Patent No.: US 9,745,366 B2
(45) Date of Patent: Aug. 29, 2017

(54) COMPOSITIONS AND METHODS FOR THE PREVENTION OF MICROBIAL INFECTIONS

(71) Applicants: University of Southern California, Los Angeles, CA (US); Research Institute at Nationwide Children's Hospital, Columbus, OH (US)

(72) Inventors: Steven D. Goodman, Hilliard, OH (US); Sheryl S. Justice, Westerville, OH (US)

(73) Assignees: University of Southern California, Los Angeles, CA (US); Research Institute at Nationwide Children's Hospital, Columbus, OH (US)

(*) Notice: Subject to any disclaimer, the term of this patent is extended or adjusted under 35 U.S.C. 154(b) by 0 days.

(21) Appl. No.: 14/493,051

(22) Filed: Sep. 22, 2014

(65) Prior Publication Data

US 2015/0086542 A1    Mar. 26, 2015

Related U.S. Application Data

(60) Provisional application No. 61/881,317, filed on Sep. 23, 2013.

(51) Int. Cl.
| A61K 39/395 | (2006.01) |
| A61K 49/00 | (2006.01) |
| A61K 39/40 | (2006.01) |
| C07K 16/12 | (2006.01) |
| C12Q 1/18 | (2006.01) |

(52) U.S. Cl.
CPC ........... *C07K 16/12* (2013.01); *C12Q 1/18* (2013.01); *C07K 2317/76* (2013.01); *G01N 2500/04* (2013.01); *G01N 2500/10* (2013.01)

(58) Field of Classification Search
CPC ............. A61K 51/10; A61K 51/1009; A61K 2039/00; C07K 16/00; C07K 16/12
See application file for complete search history.

(56) References Cited

U.S. PATENT DOCUMENTS

| 6,846,651 B2 | 1/2005 | Fleischmann et al. |
| 7,413,868 B2 | 8/2008 | Kauvar et al. |
| 7,939,344 B2 | 5/2011 | Kauvar et al. |
| 8,999,291 B2 * | 4/2015 | Goodman ............ A61K 38/164 424/184.1 |
| 2002/0132753 A1 | 9/2002 | Rosen et al. |
| 2003/0060410 A1 | 3/2003 | Tracey et al. |
| 2003/0099602 A1 | 5/2003 | Levin et al. |
| 2003/0229065 A1 | 12/2003 | Levy et al. |
| 2004/0202670 A1 | 10/2004 | Apicella |
| 2005/0131222 A1 | 6/2005 | Fleischmann et al. |
| 2005/0221439 A1 | 10/2005 | Bakaletz et al. |
| 2006/0030539 A1 | 2/2006 | Nick et al. |
| 2006/0121047 A1 | 6/2006 | Tracey |
| 2006/0228384 A1 | 10/2006 | Eldridge |
| 2006/0240045 A1 | 10/2006 | Berthet et al. |
| 2007/0154529 A1 | 7/2007 | Bullerdiek |
| 2010/0291177 A1 | 11/2010 | Hermans et al. |
| 2011/0236306 A1 | 9/2011 | Goodman et al. |
| 2012/0128701 A1 | 5/2012 | Goodman et al. |
| 2015/0166641 A1 | 6/2015 | Goodman et al. |
| 2016/0175440 A1 | 6/2016 | Goodman et al. |

FOREIGN PATENT DOCUMENTS

| WO | WO 00/47104 A2 | 8/2000 |
| WO | WO 03/026691 A2 | 4/2003 |
| WO | WO 2004/014418 A2 | 2/2004 |
| WO | WO 2004/044001 A2 | 5/2004 |
| WO | WO 2004/072094 A2 | 8/2004 |
| WO | WO 2005/025604 A2 | 3/2005 |
| WO | WO 2006/017816 A2 | 2/2006 |
| WO | WO 2006/083301 A2 | 8/2006 |
| WO | WO 2006/114805 A2 | 11/2006 |
| WO | WO 2007/001422 A2 | 1/2007 |
| WO | WO 2011/123396 A1 | 10/2011 |
| WO | WO-2012/034090 | 3/2012 |
| WO | WO 2014/201305 A1 | 12/2014 |

OTHER PUBLICATIONS

Brandstetter, K.A. et al. (2013) "Antibodies Directed Against Integration Host Factor Mediate Biofilm Clearance From Nasopore," The Laryngoscope 123(11):2626-2632.
Brockson, M.E. et al. (2014) "Evaluation of the kinetics and mechanism of action of anti-integration host factor-mediated disruption of bacterial biofilms," Molecular Microbiology 93(6):1246-1258.
Brockson, M.E. et al. (2014) "Evaluation of the kinetics and mechanism of action of anti-integration host factor-mediated disruption of bacterial biofilms," Molecular Microbiology 93(6):1246-1258: Supplementary Material, 6 pages.
Govan, J.R. et al. (1996) "Microbial pathogenesis in cystic fibrosis: mucoid Pseudomonas aeruginosa and Burkholderia cepacia," Microbiol. Rev. 60(3):539-574.
Gustave, J.E. et al. (2013) "Targeting bacterial integration host factor to disrupt biofilms associated with cystic fibrosis," Journal of Cystic Fibrosis 12(4):384-389.
Novotny, L.A. et al. (2013) "Structural Stability of Burkholderia cenocepacia Biofilms is Reliant on eDNA Structure and Presence of a Bacterial Nucleic Acid Binding Protein," PLOS ONE 8(6):e67629, 15 pages.
Whitchurch, C.B. et al. (2002) "Extracellular DNA Required for Bacterial Biofilm Formation," Science 295(5559):1487.

(Continued)

*Primary Examiner* — Rodney P Swartz
(74) *Attorney, Agent, or Firm* — Foley & Lardner LLP; Antoinette F. Konski; Natasha Iyer

(57) ABSTRACT

This disclosure provides methods and compositions to inhibit or prevent infection of a cell by a bacteria that exports DNABII proteins by administering to a tissue infected with the bacteria an effective amount of an antibody that specifically recognizes and binds the DNABII proteins, thereby inhibiting or preventing infection of the bacteria. Treatment methods, screens and kits are further provided.

18 Claims, 7 Drawing Sheets

(56) References Cited

OTHER PUBLICATIONS

Whitchurch, C.B. et al. (2002) "Extracellular DNA Required for Bacterial Biofilm Formation," Science 295(5559):1487: Supplementary Material, 2 pages.
Adams, L. et al. (2007) "Epitope-Mapping the Immune Response of Children with Otitis Media and Adults with Chronic Obstructive Pulmonary Disease to the PilA Protein of the Nontypeable *Haemophilus influenzae* Type IV Pilus," $107^{th}$ General Meeting, American Society for Microbiology, 2007, Toronto. ON.
U.S. Appl. No. 14/535,254, filed Nov. 6, 2014, University of Southern California et al.
Adams, L. et al. (2007) "Epitope-mapping the immune response of children with otitis media and adults with chronic obstructive pulmonary disease to the PilA Protein of the nontypeable *Haemophilus influenzae* Type IV pilus," $9^{th}$ International Symposium on Recent Advances in Otitis Media, St. Pete Beach, FL.
Andersson, U. et al. (2011) "HMGB1 is a Therapeutic Target for Sterile Inflammation and Infection," Annu. Rev. Immunol. 29:139-162.
Bakaletz, L.O. et al. (1997) "Relative immunogenicity and efficacy of two synthetic chimeric peptides of fimbrin as vaccinogens against nasopharyngeal colonization by nontypeable *Haemophilus influenzae* in the chincilla," Vaccine 15(9) 955-961.
Bakaletz, L.O. et al. (1999) "Protection against Development of Otitis Media Induced by Nontypeable *Haemophilus influenzae* by Both Active and Passive Immunization in a Chinchilla Model of Virus-Bacterium Superinfection," Infecion and Immunity 67(6): 2746-2762.
Barve, M.P. et al. (2003) "Cloning and characterization of the mating type (MAT) locus from *Ascochyta rabiei* (teleomorph: *Didymella rabiei*) and a *MAT* phylogeny of legume-associated *Ascochyta* spp.," Fungal Genetics and Biology 39(2):151-167.
Cho, J.H. et al. (2001) "The modulation of the biological activities of mitochondrial histone Abf2p by yeast PKA and its possible role in the regulation of mitochondrial DNA content during glucose repression," Biochimica et Biophysica Acta 1522(3):175-186.
Cohavy, O. et al. (1999) "Identification of a Novel Mycobacterial Histone H1 Homologue (HupB) as an Antigenic Target of pANCA Monoclonal Antibody and Serum Immunoglobulin A from Patients with Cohn's Disease," Infection and Immunity 67(12):6510-6517.
Estrela, A.B. et al. (2010) "Combining Biofilm-Controlling Compounds and Antibiotics as a Promising New Way to Control Biofilm Infections," Pharmaceuticals 3:1374-1393.
Falciola, L. et al. (1994) "Mutational analysis of the DNA binding domain A of chromosomal protein HMG1." Nucleic Acids Research 22(3):285-292.
Gerstel, U. et al. (2003) "Complex regulation of *csgD* promoter activity by global regulatory proeteins," Molecular Microbiology 49(3):639-654.
Goodman, S.D. et al. (1999) "Replacement of Integration Host Factor Protein-induced DNA Bending by Flexible Regions of DNA." The Journal of Biological Chemistry 274(52):37004-37011.
Goodman, S.D. et al. (2011) "Biofilms can be dispersed by focusing the immune system on a common family of bacterial nucleoid-associated proteins," Mucosal Immunology 4(6):625-637.
Greenspan, N.S. et al. (1999) "Defining epitopes: It's not as easy as it seems," Nature Biotechnology 17:936-937.
Granston, A.E. et al. (1993) "Characterization of a Set of Integration Host Factor Mutants Deficient for DNA Binding." J. Mol. Biol 234:45-59.
Hall-Stoodley, L. et al. (2008) "Characterization of biofilm matrix, degradation by DNase treatment and evidence of capsule downregulation in *Streptococcus pneumoniae* clinical isolates," BMC Microbiology 8:173, 16 pages.
Hall-Stoodley, L. et al. (2009) "Evolving concepts in biofilm infections," Cellular Microbiology 11(7):1034-1043.
Harley, V.R. et al. (2003) "The Molecular Action and Regulation of the Testis-Determining Factors, SRY (Sex-Determining Region on the Y Chromosome) and SOX9 [SRY-Related High-Mobility Group (HMG) Box 9]." Endocrine Reviews 24(4):466-487.
Haruta, I. et al. (2008) "A possible role of histone-like DNA-binding protein of *Streptococcus intermedius* in the pathogenesis of bile duct damage in primary biliary cirrhosis," Clinical Immunology 127:245-251.
Jodar, L. et al. (2002) "Development of vaccines against meningococcal disease," Lancet 359:1499-1508.
Jurcisek. J.A. et al. (2007) "Biofilms Formed by Nontypeable *Haemophilus influenzae* In Vivo Contain both Double-Stranded DNA and Type IV Pilin Protein," Journal of Bacteriology 189(10): 3868-3875.
Kamashev, D. et al. (2000) "The histone-like protein HU binds specifically to DNA recombination and repair intermediates," The EMBO Journal 19(23):6527-6535.
Kennedy. B-J. et al. (2000) "Passive Transfer of Antiserum Specific for Immunogens Derived from a Nontypeable *Haemophilus influenzae* Adhesin and Lipoprotein D Prevents Otitis Media After Heterologous Challenge." Infection and Immunity 68(5):2756-2765.
Kornblit. B. et al. (2007) "The genetic variation of the human HMG1 gene," Tissue Antigens 70:151-156.
Kyd. J.M. et al. (2003) "Efficacy of the 26-Kilodaiton Outer Membrane Protein and Two P5 Fimbrin-Derived Immunogens To Induce Clearance of Nontypeable *Haemophilus influenzae* from the Rat Middle Ear and Lungs as Well as from the Chinchilla Middle Ear and Nasopharynx." Infection and Immunity 71(8):4691-4699.
Labbe. E. et al. (2000) "Association of Smads with lymphoid enhancer binding factor 1/T cell-specific factor mediates cooperative signaling by the transforming growth factor-β and Wnt pathways," Proc. Natl. Acad. Sci. USA 97(15):8358-8363.
Li, L. et al. (2000) "Retroviral cDNA Integration: Stimulation by HMG I Family Proteins," Journal of Virology 74(23):10965-10974.
Melulani, G.J. et al. (1995) "Mucoid Pseudomonas aeruginosa Growing in a Biofilm In Vitro Are Killed by Opsonic Antibodies to the Mucoid Exopolysaccharide Capsule but Not by Antibodies Produced During Chronic Lung Infection in Cystic Fibrosis Patients," The Journal of Immunology 155:2029-2038.
Mouw, K.W. et al. (2007) "Shaping the *Borrelia burgdorferi* genome: crystal structure and binding properties of the DNA-bending protein Hbb." Molecular Microbiology 63(5):1319-1330.
Murphy, T.F. et al. (2009) "Microbial Interactions in the Respiratory Tract," The Pediatric Infectious Disease Journal 28:S121-S126.
Nakamura. Y. et al. (2001) "HMG Box A in HMG3 Protein Functions as a Mediator of DNA Structural Alteration Together with Box B," J. Biochem. 1129:643-651.
Nash. H.A. et al. (1987) "Overproduction of *Escherichia coli* integration Host Factor. a Protein with Nonidentical Subunits," Journal of Bacteriology 169(9):4124-4127.
NCBI Genebank: P0A6Y1 (Sep. 13, 2005).
Novotny, L.A. et al. (2000) "Epitope mapping of the Outer Membrane Protein P5-Homologous Fimbrin Adhesin of Nontypeable *Haemophilus influenzae*," Infection and Immunity 68(4):2119-2128.
Novotny, L.A. et al. (2002) "Detection and characterization of pediatric serum antibody to the OMP P5-homologous adhesin of nontypeable *Haemophilus influenzae* during acute otitis media," Vaccine 20(29-30):3590-3597.
Novotny, L.A. et al. (2003) "The Fourth Surface-Exposed Region of the Outer Membrane Protein P5-Homologous Adhesin of the Nontypable *Haemophilus influenzae* Is an Immunodominant But Nonprotective Decoying Epitope," The Journal of Immunology 171(4):1978-1983.
Novotny, L.A. et al. (2006) "Passive immunization with human anti-protein D antibodies induced by polysaccharide protein D conjugates protects chinchillas against otitis media after intranasal challenge with *Haemophilus influenzae*," Vaccine 24(22):4804-4811.
Novotny, L.A. et al. (2010) "Epitope mapping immunodominant regions of the PilA protein of nontypeable *Haemophilus influenzae* (NTHI) to facilitate the design of two novel chimeric vaccine candidates," Vaccine 28(1):279-289.
Oberto, J. et al. (1994) "Histones, HMG, HU, IHF: Mème combat," Biochimie 76:901-908.

(56) References Cited

OTHER PUBLICATIONS

Ordway, D.J. et al. (2010) "Evaluation of Standard Chemotherapy in the Guinea Pig Model of Tuberculosis." Antimicrobial Agents and Chemotherapy 54:1820-1833.
Otto. J. (2009) "*Staphylococcus epidermidis*—the 'accidental' pathogen," Nature Reviews Microbiology 7:555-567.
Pedulla. M.L. et al. (1996) "A novel host factor for integration of mycobacteriophage L5," Proc. Natl. Acad. Sci. USA 93:15411-15416.
Prymulal R. et al. (2006) "Pneumococcal capsular polysaccharides conjugated to protein D for prevention of acute otitis media caused by both *Streptococcus pneumoniae* and non-typable *Haemophilus influenzae*: a randomized double-blind efficacy study." Lancet 367(9512):740-748.
Rice, P.A. et al. (1996) "Crystal Structure of an IHF-DNA Complex: A Protein-Induced DNA U-Turn," Cell 87(7):1295-1306.
Sapi. E. et al. (2012) "Characterization of Biofilm Formation by *Borrelia burgdorferi* In Vitro," PLOS One 7(10):e44277, 1-11.
Schwartz, K. et al. (2012) "Functional Amyloids Composed of Phenol Soluble Modulins Stabilize *Staphylococcus aureus* Biofilms." PLOS Pathogens 8:e1002744. 1-11.
Skolnick, J. et al. (2000) "From genes to protein structure and function: novel applications of computational approaches in the genomic era." Trends in Biotechnology 18:34-39.
Stinson, M.W. et al. (1998) "Streptococcal Histone-Like Protein: Primary Structure of *hipA* and Protein Binding to Lipoteichoic Acid and Epithelial Cells," Infection and Immunity 66(1):259-265.
Stoltz, D.A. et al. (2010) "Cystic Fibrosis Pigs Develop Lung Disease and Exhibit Defective Bacterial Eradication at Birth." www.ScienceTranslationMedicine.org 2(29)29ra31:1-8.
Stros, M. et al. (2007) "The HMG-box: a versatile protein domain occurring in a wide variety of DNA-binding proteins." Cell. Mol. Life Sci. 64(19-20):2590-2606.
Swinger, K.K. et al. (2004) "IHF and HU: flexible architects of bent DNA." Current Opinion in Structural Biology 14:28-35.
Taudte, S. et al. (2000) "Alanine mutagenesis of high-mobility-group-protein-1 box B (HMG1-B)," Biochem. J. 347:807-814.
Tetz, G.V. et al. (2009) "Effect of DNase and Antibiotics on Biofilm Characteristics," Antimicrobial Agents and Chemotherapy 53(3):1204-1209.
Thomas, J.O. (2001) "HMG1 and 2: architectural DNA-binding proteins." Biochemical Society Transactions 29(Pt 4):395-401.
Winther, B. et al. (2009) "Location of Bacterial Biofilm in the Mucus Overlying the Adenoid by Light Microscopy," Head & Neck Surgery 135(12):1239-1245.
Restriction Requirement in U.S. Appl. No. 13/073,782, dated Feb. 20, 2013, 10 pages.
Non-Final Office Action in U.S. Appl. No. 13/073,782, dated Jun. 10, 2013, 15 pages.
Final Office Action in U.S. Appl. No. 13/073,782, dated Mar. 27, 2014, 8 pages.
Non-Final Office Action in U.S. Appl. No. 13/073,782, dated Jun. 25, 2014, 5 pages.
Notice of Allowance in U.S. Appl. No. 13/073,782, dated Aug. 19, 2014, 11 pages.
Restriction Requirement in U.S. Appl. No. 13/229,575, dated Jul. 19, 2012, 9 pages.
Non-Final Office Action in U.S. Appl. No. 13/229,575, dated Jan. 10, 2013. 18 pages.
Final Office Action in U.S. Appl. No. 13/229,575. dated Aug. 29, 2013, 17 pages.
Non-Final Office Action in U.S. Appl. No. 13/229,575, dated Mar. 31, 2014, 32 pages.
Final Office Action in U.S. Appl. No. 13/229,575, dated Sep. 19, 2014, 34 pages.
Martinez-Antonio A et al. (2008), "Functional organization of *Escherichia coli* transcriptional regulatory network", J. Mol. Biol. vol. 381, p. 238-247.
Seikagaku [Biochemistry], 1996, vol. 68, No. 12, pp. 1829-1834.

Hall-Stoodley et al., "Evolving concepts in biofilm infections", Cellular Microbiology, vol. 11, No. 7, p. 1034-1043, 2009.
Notice of Allowability for U.S. Appl. No. 13/073,782, mailed Mar. 4, 2015, 4 pages.
Restriction Requirement for U.S. Appl. No. 14/535,254, mailed Mar. 27, 2015, 8 pages.
U.S. Appl. No. 13/229,575, filed Sep. 9, 2011, Goodman et al.
Non-Final Office Action for U.S. Appl. No. 14/535,254, mailed Sep. 9, 2015.
U.S. Appl. No. 14/885,800, filed Oct. 16, 2015, Goodman et al.
Final Office Action for U.S. Appl. No. 14/535,254, mailed Mar. 25, 2016.
U.S. Appl. No. 15/078,987, filed Mar. 23, 2016, Research Institute at Nationwide Children's Hospital.
Bakaletz, L.O., Biofilms can be dispersed by focusing the immune system on a common family of bacterial nucleoid associated proteins, 6th ASM Conference on Biofilms, Miami, FL, Sep. 29-Oct. 4, 2012 (presentation).
Bakaletz, L.O., Targeting the biofilm for development of novel preventative and therapeutic vaccine candidates to prevent otitis media, 6th ASM Conference on Biofilms, Miami, FL, Sep. 29-Oct. 4, 2012 (presentation).
Beech, I.B. et al. (2005) "Microbe-surface interactions in biofouling and biocorrosion processes," International Microbiology 8:157-168.
Bjarnsholt, T. (2013) "The role of bacterial biofilms in chronic infections," APMIS 121(Suppl. 136):1-51.
Boles, B.R. et al. (2011) "Staphylococcal biofilm disassembly," Trends in Microbiology 19(9):449-455.
Brady, R.A. et al. (2006) "Identification of *Staphylococcus aureus* Proteins Recognized by the Antibody-Mediated Immune Response to a Biofilm Infection," Infection and Immunity 74(6):3415-3426.
Catlin, B.W. (1956) "Extracellular Deoxyribonucleic Acid of Bacteria and a Deoxyribonuclease Inhibitor," Science 124:441-442.
Ceri, H. et al. (1999) "The Calgary Biofilm Device: New Technology for Rapid Determination of Antibiotic Susceptibilities of Bacterial Biofilms," Journal of Clinical Microbiology 37(6):1771-1776.
Chen, C. et al. (2004) "Substrate specificity of Helicobacter pylori histone-like HU protein is determined by insufficient stabilization of DNA flexure points," Biochem J. 383:343-351.
Coenye, T. et al. (2010) "In vitro and in vivo model systems to study microbial biofilm formation," Journal of Microbiological Methods 83:89-105.
Collarini, E.J. et al. (2009) "Potent High-Affinity Antibodies for Treatment and Prophylaxis of Respiratory Syncytial Virus Derived from B Cells of Infected Patients," J Immunol 183:6338-6345.
Dalai, B. et al. (2009) "Histone-like protein H—NS regulates biofilm formation and virulence of Actinobacillus pheuropneumonia," Microbial Pathogenesis 46:128-134.
Darouiche, R.O. et al. (2004) "Treatment of Infections Associated with Surgical Implants," N Engl J Med 350:1422-1429.
Dominguez-Herrera, J. et al. (2011) "Efficacy of Daptomycin versus Vancomycin in an Experimental Model of Foreign-Body and Systemic Infection Caused by Biofilm Producers and Methicillin-Resistant *Staphylococcus epidermidis*," Antimicrobial Agents and Chemotherapy 56(2):613-617.
Donlan, R.M. et al. (2002) "Biofilms: Survival Mechanisms of Clinically Relevant Microorganisms," Clinical Microbiology Reviews 15(2):167-193.
Durocher, Y. et al. (2002) "High-level and high-throughput recombinant protein production by transient transfection of suspension-growing human 293-EBNA1 cells," Nucleic Acids Research 30(2):e9, 1-9.
Eboigbodin, K.E. et al. (2008) "Characterization of the Extracellular Plymeric Substances Produced by *Escherichia coli* Using Infrared Spectroscopic, Proteomic, and Aggregation Studies," Biomacromolecules 9:686-695.
Fedorov, O. et al. (2012) "Kinase Inhibitor Selectivity Profiling Using Differential Scanning Fluorimetry," Kinase Inhibitors: Methods and Protocols, Methods in Molecular Biology 795:109-118.
Garcia-Contreras, R. et al. (2008) "Protein Translation and Cell Death: The Role of Rare tRNAs in Biofilm Formation and in Activating Dormant Phage Killer Genes," PLoS ONE 3(6):e2394, 1-15.

(56) References Cited

OTHER PUBLICATIONS

Goodman, S.D. et al. (1999) "In Vitro Selection of Integration Host Factor Binding Sites," Journal of Bacteriology 181(10):3246-3255.
Goodman, S.D., A new immunotherapeutic approach that disperses biofilms, Banff Conference on Infectious Diseases, Banff, Alberta, Canada, May 18, 2012 (presentation).
Goodman, S.D., Nucleoprotein complexes in the extracellular matrix are critical for the structural integrity of bacterial biofilms, 112th General Meeting, American Society for Microbiology, San Francisco, CA, Jun. 18, 2012 (presentation).
Gustave et al., Biofilms recovered from the sputum of CF patients contain the bacterial protein integration host factor (IHF), 25th Annual North American Cystic Fibrosis Conference, Anaheim, CA, Nov. 3-5, 2011 (poster).
Gustave et al., Biofilms recovered from the sputum of CF patients contain the bacterial protein integration host factor (IHF), Abst. 25th Annual North American Cystic Fibrosis Conference, Anaheim, CA, Nov. 3-5, 2011.
Hall-Stoodley, L. et al. (2004) "Bacterial Biofilms: From the Natural Environment to Infectious Diseases," Nature Reviews, Microbiology 2:95-108.
Hall-Stoodley, L. et al. (2006) "Direct Detection of Bacterial Biofilms on the Middle-Ear Mucosa of Children With Chronic Otitis Media," JAMA 296(2):202-211.
Haluzi, H. et al. (1991) "Genes Coding for Integration Host Factor Are Conserve in Gram-Negative Bacteria," Journal of Bacteriology 173(19):6297-6299.
Harriman, W.D. et al. (2008) "Antibody discovery via multiplexed single cell characterization," Journal of Immunological Methods 341:135-145.
Harrison, J.J. et al. (2010) "Microtiter susceptibility testing of microbes growing on peg lids: a miniaturized biofilm model for high-throughput screening," Nature Protocols 5(7):1236-1254.
Haruta, I. et al. (2010) "Long-term bacterial exposure can trigger nonsuppurative destructive cholangitis associated with multifocal epithelial inflammation," Laboratory Investigation 90:577-588.
Hoyle, B. et al. (1991) "Bacterial Resistance to Antibiotics: The Role of Biofilms," Prog. Drug Res. 37:91-105.
Janeway, C.A. et al. (2001) "Manipulating the immune response to fight infection," Immunobiology: The Immune System in Health and Disease, 5th ed.; retrieved online from https://www.ncbi.nlm.nih.gov/books/NBK27131/.
Jiao, Y. et al. (2011) "Identification of Biofilm Matrix-Associated Proteins from an Acid Mine Drainage Microbial Community," Appl & Environ Microbiol. 77:5230-5237.
John, A-K. et al. (2011) "Reversible Daptomycin Tolerance of Adherent Staphylococci in an Implant Infection Model," Antimicrobial Agents and Chemotherapy 55(7):3510-3516.
Johnson, R. et al. (2008) "Chapter 8: Bending and Compaction of DNA by Proteins," Protein-Nucleic Acid Interactions: Structural Biology:176-220.
Joo, H-S. et al. (2012) "Molecular Basis of In Vivo Formation by Bacterial Pathogens," Chemistry & Biology 19:1503-1513.
Jurcisek, J. et al. (2005) "Role of Sialic Acid and Complex Carbohydrate Biosynthesis in Biofilm Formation by Nontypeable Haemophilus influenzae in the Chinchilla Middle Ear," Infection and Immunity 73:3210-3218.
Justice, S.S. et al. (2012) "Aberrant Community Architecture and Attenuated Persistence of Uropathogenic Escherichia coli in the Absence of Individual IHF Subunits," PLoS ONE 7(10):e48349, 1-11.
Khrapunov, S. et al. (2006) "Binding then bending: A mechanism for wrapping DNA," PNAS 103(51):19217-19218.
Kim, N. et al. (2002) "Proteins Released by Helicobacter pylori In Vitro," Journal of Bacteriology 184(22):6155-6162.
Kristian, S.A. et al. (2003) "Alanylation of Teichoic Acids Protects Staphylococcus aureus against Toll-like Receptor 2-Dependent Host Defense in a Mouse Tissue Cage Infection Model," The Journal of Infectious Diseases 188:414-423.

Lebeaux, D. et al. (2013) "From in vitro to in vivo Models of Bacterial Biofilm-Related Infections," Pathogens 2:288-356.
Liu, D. et al. (2008) "The essentiality and involvement of Streptococcus intermedius histone-like DNA-binding protein in bacterial viability and normal growth," Molecular Microbiology 68(5):1268-1282.
Lunsford, R.D. et al. (1996) "DNA-Binding Activities in Streptococcus gordonii: Indentification of a Receptor-Nickase and a Histonelike Protein," Current Microbiology 32:95-100.
Lutz, H.U. et al. (1990) "Covalent binding of detergent-solubilized membrane glycoproteins to 'Chemobond' plates for ELISA," Journal of Immunological Methods 129:211-220.
Malhotra et al., Identification of immunoprotective domains within the bacterial DNA-binding protein, integration host factor, 20th Annual Midwest Microbial Pathogenesis Meeting. The Ohio State University, Columbus, OH, Aug. 23-25, 2013 (poster).
Malhotra et al., Identification of immunoprotective domains within the bacterial DNA-binding protein, integration host factor, Abst. 20th Annual Midwest Microbial Pathogenesis Meeting. The Ohio State University, Columbus, OH, Aug. 23-25, 2013.
Malhotra et al., Identification of immunoprotective domains within the bacterial DNA-binding protein, integration host factor, Abst. Seventh Extraordinary International Symposium on Recent Advances in Otitis Media, Stockholm, Sweden, Jun. 12, 2013.
Malhotra et al., Identification of immunoprotective domains within the bacterial DNA-binding protein, integration host factor, Seventh Extraordinary International Symposium on Recent Advances in Otitis Media, Stockholm, Sweden, Jun. 15, 2013 (presentation).
Mann, E.E. et al. (2009) "Modulation of eDNA Release and Degradation Affects Staphylococcus aureus Biofilm Maturation," PLoS ONE 4(6):e5822, 1-12.
Mukherjee, J. et al. (2011) "Quantitative protein expression and cell surface characteristics of Escherichia coli MG1655 biofilms," Proteomics 11:339-351.
Murphy, T.F. et al. (2002) "Biofilm formation by nontypeable Haemophilus influenzae: strain variablitiy, outer membrane antigen expression and role of pili," BMC Microbiology 2:7, 1-8.
Non-Final Office Action in U.S. Appl. No. 14/535,254, mailed Aug. 12, 2016.
Non-Final Office Action in U.S. Appl. No. 14/885,800, mailed Oct. 31, 2016.
Non-Final Office Action in U.S. Appl. No. 15/078,987, mailed Jul. 14, 2016.
PDB ID: 1 IHF: Rice, P.A. et al. (1996), 1 page; retrieved online from http://www.rcsb.org/pdb/explore.do?structureId=IHF.
Petersen, F.C. et al. (2004) "Biofilm Mode of Growth of Streptococcus intermedius Favoreed by a Competence-Stimulating Signaling Peptide," Journal of Bateriology 186(18):6327-6331.
Pethe, K. et al. (2001) "Mycobacterium smegmatis laminin-binding glycoprotein shares epitopes with Mycobacterium tuberculosis heparin-binding haemagglutinin," Molecular Microbiology 39(1):89-99.
Rudikoff, S. et al. (1982) "Single amino acid substitution altering antigen-binding specificity," Proc. Natl. Acad. Sci. USA 79(6):1979-1983.
Segall, A.M. et al. (1994) "Architectural elements in nucleoprotein complexes: interchangeability of specific and non-specific DNA binding proteins," The EMBO Journal 13(19):4536-4548.
Shahrooei, M. et al. "Inhibition of Staphylococcus epidermidis Biofilm Formation by Rabbit Polyclonal Antibodies against the SesC Protein," Infection and Immunity 77(9):3670-3678.
Shields, R.C. et al. (2013) "Efficacy of a Marine Bacterial Nuclease against Biofilm Forming Microorganisms Isolated from Chronic Rhinosinusitis," PLoS ONE 8(2):e55339, 1-13.
Singh, P.K. et al. (2000) "Quorum-sensing signals indicate that cystic fibrosis lungs are infected with bacterial biofilms," Nature 407(12):762-764.
Sun, D. et al. (2005) "Inhibition of Biofilm Formation by Monoclonal Antibodies against Staphylococcus epidermidis RP62A Accumulation-Associated Protein," Clinical & Diagnostic Labroratory Immunology 12(1):93-100.

(56) References Cited

OTHER PUBLICATIONS

Teter, B. et al. (2000) "DNA Bending and Twisting Properties of Integration Host Factor Determined by DNA Cyclization," Plasmid 43:73-84.

Tsaras, G. et al. (2012) "Incidence, Secular Trends, and Outcomes of Prosthetic Joint Infection: A Population-Based Study, Olmsted County, Minnesota, 1969-2007," Infect Control Hosp Epidemiol 33(12):1207-1212.

Van Schaik, E.J. et al. (2005) "DNA Binding: a Novel Function of Pseudomonas aeruginosa Type IV Pili," Journal of Bacteriology 187(4):1455-1464.

Winters, B.D. et al. (1993) "Isolation and Characterization of a *Streptococcus pyogenes* Protein that Binds to Basal Laminae of Human Cardiac Muscle," Infection and Immunity 61(8):3259-3264.

Zimmerli, W. et al. (1982) "Pathogenesis of Foreign Body Infection: Description and Characteristics of an Animal Model," The Journal of Infectious Diseases 146(4):487-497.

Zimmerli, W. et al. (1984) "Pathogenesis of Foreign Body Infection," J. Clin. Invest. 73:1191-1200.

Final Office Action in U.S. Appl. No. 15/078,987, dated Dec. 28, 2016.

Liu, D. et al. (2008) "Histone-like DNA binding protein of *Streptococcus intermedius* induces the expression of pro-inflammatory cytokines in human monocytes via activation of ERK1/2 and JNK pathways," Cellular Microbiology 10(1):262-276.

Bass, J.I.F. et al. (2010) "Extracellular DNA: A Major Proinflammatory Component of *Pseudomonas aeruginosa* Biofilms," The Journal of Immunology 184:6386-6395.

Fan, Z. et al. (2002) "HMG2 Interacts with the Nucleosome Assembly Protein SET and Is a Target of the Cytotoxic T-Lymphocyte Protease Granzyme A," Molecular and Cellular Biology 22(8):2810-2820.

Final Office Action in U.S. Appl. No. 14/885,800, dated May 4, 2017.

Non-Final Office Action in U.S. Appl. No. 14/967,228, dated May 19, 2017.

Percival, S.L. et al. (2015) "Biofilms and Wounds: An Overview of the Evidence," Advances in Wound Care 4(7):373-381.

Final Office Action in U.S. Appl. No. 14/535,254, dated Jun. 9, 2017.

Non-Final Office Action in U.S. Appl. No. 15/078,987, dated Jun. 14, 2017.

Non-Final Office Action in U.S. Appl. No. 14/535,254, dated Jul. 10, 2017.

Takeda, T. (2012) "Polyhistidine Affinity Chromatography for Purification and Biochemical Analysis of Fungal Cell Wall-Degrading Enzymes," Affinity Chromatography, Dr. Sameh Magdeldin (Ed.), ISBN: 978-953-51/0325-7, In Tech :177-186.

\* cited by examiner

| Strain | Dimensions (μm) | Ratio | Area (μm$^2$) |
|---|---|---|---|
| UTI89 | 46.60 x 57.68 | 1 : 1.24 | 2111.06 |
| kpsF | 32.0 x 93.8 | 1 : 2.93 | 2357.45 |
| ihfA | 40.234 x 49.619 | 1 : 1.23 | 1567.90 |
| ihfB | 19.298 x 61.669 | 1 : 3.12 | 934.70 |
| surA | 32.23 x 42.97 | 1 : 1.33 | 1087.72 |

COMPOSITIONS AND METHODS FOR THE PREVENTION OF MICROBIAL INFECTIONS

CROSS-REFERENCE TO RELATED APPLICATION

This application claims the benefit under 35 U.S.C. §119(e) to U.S. Provisional Application No. 61/881,317, filed Sep. 23, 2013, the content of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on May 20, 2015, is named 106887-6302_SL.txt and is 602 bytes in size.

TECHNICAL FIELD

This invention generally relates to the methods and compositions to prevent infection of eukaryotic cells by microbial organisms.

BACKGROUND

Throughout this application, technical and patent literature is identified by a citation or a first author and date of publication. Complete citations for the publications identified by author and date can be found in the application papers, immediately preceding the claims. The technical and patent literature are incorporated by reference into the specification to more fully describe the state of the art to which this invention pertains.

Chronic and recurrent infections result when the human body fails to clear the disease causing bacteria. One means by which bacteria persist is by invading human host cells. Once inside they are protected from the immune system and antimicrobial therapies. Moreover, these bacteria have evolved to divide and eventually kill these host cells, releasing the endogenous bacteria and allowing subsequent re-infection; this is the root cause of the chronicity of the disease state.

Many bacterial species multiply within organized communities as a part or whole of their lifestyles in the environment or in the host. Uropathogenic *Escherichia coli* (UPEC), the causative agent of up to 80% of all urinary tract infections (Foxman, B. (2010) Nat. Rev. Urol. 7:653-660), is one such species. UPEC uses a community-based developmental pathway to propagate within the cytoplasm of urothelial cells during bacterial cystitis (Justice, S. S. et al. (2004) Proc. Natl. Acad. Sci. U.S.A. 101:1333-1338; Mulvey, M. A. et al. (1998) Science 282:1494-1497; Anderson, G. G. et al. (2003) Science 301:105-107). The developmental pathway begins with attachment-mediated invasion into the superficial bladder epithelial cells via FimH binding to the mannosylated uroplakin proteins (Zhou, G. et al. (2002) Mol. Cell Proteomics 1:117-124) and involves fusiform vesicles (Bishop, B. L. et al. (2007) Nature Medicine 13, 625-630), cyclic AMP (Bishop, B. L. et al. (2007) Nature Medicine 13, 625-630), Toll-like receptor-4 (TLR4) (Song, J. et al. (2007) Cell Host Microbe 1:287-298) and integrins (Eto, D. S. et al. (2007) PLoS Pathog. 3:e100). Within the cytoplasm, bacillary-shaped UPEC multiply within loosely associated intracellular bacterial communities (IBCs) (Justice, S. S. et al. (2004) Proc. Natl. Acad. Sci. U.S.A. 101:1333-1338). IBC maturation involves both changes in cell division fidelity and community architecture, which results in coccoid-shaped UPEC in an organized, globular community architecture. Once the IBC occupies the majority of the cytoplasm, UPEC regain a bacillary shape, become motile and egress from the epithelial cell through disruptions in the cell membrane. The intracellular amplification of UPEC occurs in repetitive cycles through attachment of egressed organisms to naïve superficial epithelial cells and ultimately culminates in the establishment of a latent or chronic infection (Mulvey, M. A. et al. (2001) Infect. Immun. 69:4572-4579; Mysorekar, I. U. et al. (2006) Proc. Natl. Acad. Sci. U.S.A. 103:14170-14175; Hannan, T. J. et al. (2010) PLoS Pathog. 6(8):e1001042). Evidence for each of these stages is observed in urine samples and bladder biopsies of patients colonized with either UPEC or *Klebsiella pneumoniae* (Rosen, D. A. et al. (2007) PLoS Medicine 4:e329; Rosen, D. A. et al. (2008) Infect. Immun. 76:3337-3345), which demonstrates that these similar events comprise the pathogenic lifestyle of multiple uropathogens during cystitis.

This a need exists to stop or arrest infection of these pathogens. This invention satisfies this need and provides related advantages as well.

SUMMARY

This disclosure provides methods and compositions to inhibit or prevent infection of a host cell by a bacteria that exports members of the DNABII family of proteins, the methods and compositions comprising, or alternatively consisting essentially of, or yet further consisting of, administering to a tissue exposed to or infected with the bacteria an effective amount of an bacteria-relevant antibody that specifically recognizes and binds the DNABII proteins, thereby inhibiting or preventing infection of the host cell by the bacteria. The antibody can be polyclonal, monoclonal or a derivative of an antibody that recognizes and binds the bacteria-relevant DNABII proteins. Multiple antibodies can be administered concurrently or sequentially along with supporting therapies as noted herein. Owing to the omnipresence of these DNABII proteins associated with the bacterial surface throughout the life cycle of the cell inclusive of all states, e.g. individual, aggregated or resident biofilm bacteria, Applicants have shown that antisera directed to DNABII proteins interferes with interactions with the host cell surface including, attachment and subsequent invasion. Bacteria that can invade and propagate in host cells are protected from the host's immune system and antimicrobial therapy. Rendering bacteria incapable of binding and invasion makes them susceptible to clearance by the immune system and administered antimicrobials. The source of antibody against the DNABII family proteins can be elicited by either active vaccination of the host with proteins of the DNABII family or passive transfer of antiserum or an antibody against proteins of the DNABII family.

This disclosure provides a method to inhibit or prevent infection of a cell by a bacteria that exports a DNABII protein, e.g., HU or "histone-like protein" from *E. coli* strain U93 and an Integration Host Factor (IHF). The method comprises, or alternatively consists essentially of, or yet further consists of, administering to a tissue infected with the bacteria an effective amount of an antibody that specifically recognizes and binds the DNABII protein, thereby inhibiting or preventing infection of the bacteria. The source of antibody against the DNABII family proteins can be elicited by either active vaccination of the host with proteins of the DNABII family or passive transfer of antiserum or an antibody against proteins of the DNABII family. The antibody can be polyclonal, monoclonal or a derivative of an antibody that recognizes and binds the bacteria-relevant DNABII proteins. Multiple antibodies can be administered concurrently or sequentially along with supporting therapies as noted herein.

Integration Host Factor (IHF) and HU are members of the ubiquitous DNABII family and act as DNA architectural elements that can alter the conformation of nucleoprotein interactions inside the cell influencing replication, transcription, recombination and DNA repair (Rouviere-Yaniv, J. et al. (1975) Proc. Natl. Acad. Sci. U.S.A. 72:3428-3432; Miller, H. I. et al. (1979) Cold Spring Harbor Symp. Quant. Biol. 4(Pt 2):1121-1126; Swinger, K. K. et al. (2004) Curr. Opin. Struct. Biol. 14:28-35). IHF is required for regulation of a number of genetic loci associated with virulence. Positive activation of elastase in *Vibrio vulnificus* (Jeong, H. S. et al. (2010) The Journal of Biological Chemistry 285: 9357-9366), cholera toxin in *Vibrio cholera* (Stonehouse, E. et al. (2008) J. Bacteriol. 190:4736-4748), and type III secretion effectors in *E. coli* (Li, M. et al. (2004) Appl. Environ. Microbiol. 70:5274-5282) require IHF. IHF enhances persistence of *Legionella pneumophila* in the protist host *Acanthamoeba castellanii* (Morash, M. G. et al. (2009) Appl. Environ. Microbiol. 75:1826-1837). Regulation of adhesins and capsule is also IHF-dependent in *Neisseria* (Hill, S. A. et al. (2002) Mol. Cell. Probes 16:153-158) and *E. coli* (Rowe, S. et al. (2000) J. Bacteriol. 182:2741-2745; Corcoran, C. P. et al. (2009) Mol. Microbiol. 74:1071-1082). Accordingly, non-limiting examples of bacteria that export DNABII include *Vibrio vulnificus, Vibrio cholera, E. coli, Legionella pneumophila, Neisseria*.

The administration can be in vitro in a culture or in vivo, by administration to a patient infected with the bacteria. When practiced in vivo, the method can be used to treat a subject infected with the bacteria by administering to the infected subject an effective amount of the antibody. In addition, when the subject is a non-human animal, the method can be used to test possible therapies or combination therapies prior to administration to a human. When practiced in vitro, the method is useful to screen for other therapeutic agents and combination therapies, such as small molecule drugs, that inhibit or prevent infection of the bacteria in a tissue.

Also provided are methods to treat a bacterial infection in subject in need thereof, wherein the subject is infected with a bacteria that is a member of the DNABII family, the method comprising, or alternatively consisting essentially of, or yet further consisting of, administering to the subject an effective amount of an antibody that specifically recognizes and binds the DNABII family members, thereby inhibiting or preventing infection of the bacteria. The antibody can be polyclonal, monoclonal or a derivative of an antibody that recognizes and binds the bacteria-relevant DNABII proteins. The source of antibody against the DNABII family proteins can be elicited by either active vaccination of the host with proteins of the DNABII family or passive transfer of antiserum or an antibody against proteins of the DNABII family. Multiple antibodies can be administered concurrently or sequentially along with supporting therapies as noted herein.

Yet further provided are methods to treat a condition in a subject in need thereof, wherein the condition is associated with a bacterial infection wherein the bacteria is a DNABII family member, the method comprising, or alternatively consisting essentially of, or yet further consisting of, administering to the subject an effective amount of an antibody that specifically recognizes and binds the DNABII protein, thereby inhibiting or preventing infection of the bacteria. The source of antibody against the DNABII family proteins can be elicited by either active vaccination of the host with proteins of the DNABII family or passive transfer of antiserum or an antibody against proteins of the DNABII family. The antibody can be polyclonal, monoclonal or a derivative of an antibody that recognizes and binds the bacteria-relevant DNABII proteins. Multiple antibodies can be administered concurrently or sequentially along with supporting therapies as noted herein.

Any of the above methods can further comprise, or alternatively consist essentially of, or yet further consist of, administering to the subject or the tissue or cell culture in vitro, an effective amount of one or more of an antimicrobial, an antigenic peptide or an adjuvant. The subject, in some aspects, is a non-human animal or a human patient.

The antibody, polypeptide or composition is administered locally or systemically by any appropriate method, e.g., to the site of infection, topically, rectally, vaginally, ocularly, subcutaneous, intramuscularly, intraperitoneally, urethrally, intranasally, by inhalation or orally.

In some aspects, the subject is a pediatric patient and the antibody is administered in a formulation for the pediatric patient.

A screen to identify potential therapeutic agents that inhibit or prevent infection of a cell by a bacteria that exports an DNABII protein is also disclosed. The screening method comprises, or alternatively consists essentially of, or yet consists of, contacting in vitro or administering in vivo to a tissue infected with the bacteria an agent and determining if the agent binds the DNAB II protein. Methods to determining binding are known in the art and several non-limiting examples are described herein. In one aspect, if the agent binds the protein, the agent is a potential therapeutic agent and if the agent does not bind the protein, the agent is not a potential therapeutic agent. In another aspect, if the infection is inhibited or prevented in vivo, the agent is a potential therapeutic agent and if infection is not inhibited or prevented, the agent is not a potential therapeutic agent. Methods to determining if the infection is inhibited or prevented are known in the art and several non-limiting examples are described herein. Non-limiting examples of potential therapeutic agents are from the group of: an antibody, an antibody derivative, a polypeptide or a small molecule. Multiple antibodies can be administered concurrently or sequentially along with supporting therapies as noted herein. In a further aspect, the agent binds the protein and the binding is compared to the binding of anti-DNABII antisera to the protein, e.g., antisera directed against IhfAB.

Kits are further provided which contain the compositions described herein, e.g., an antibody and instructions for intended use.

BRIEF DESCRIPTION OF THE FIGURES

FIGS. 4A and 4B show quantitative Assessment of Intracellular Bacteria. The individual statistics of the bacteria growing within bladder epithelial cells (A) The cell length of each bacterium was evaluated within individual images (NIH image J) or 3-dimensional rendering (Dabdoub, S. et al. (2012) Visual Analytics in Healthcare (in press)). The cell length distribution for each strain is represented. (B) The maximum dimension in the x and y axes, the ratio of the axes as well as the overall area of the intracellular bacteria were determined using Prokarymetrics.

DETAILED DESCRIPTION

Figure 1:
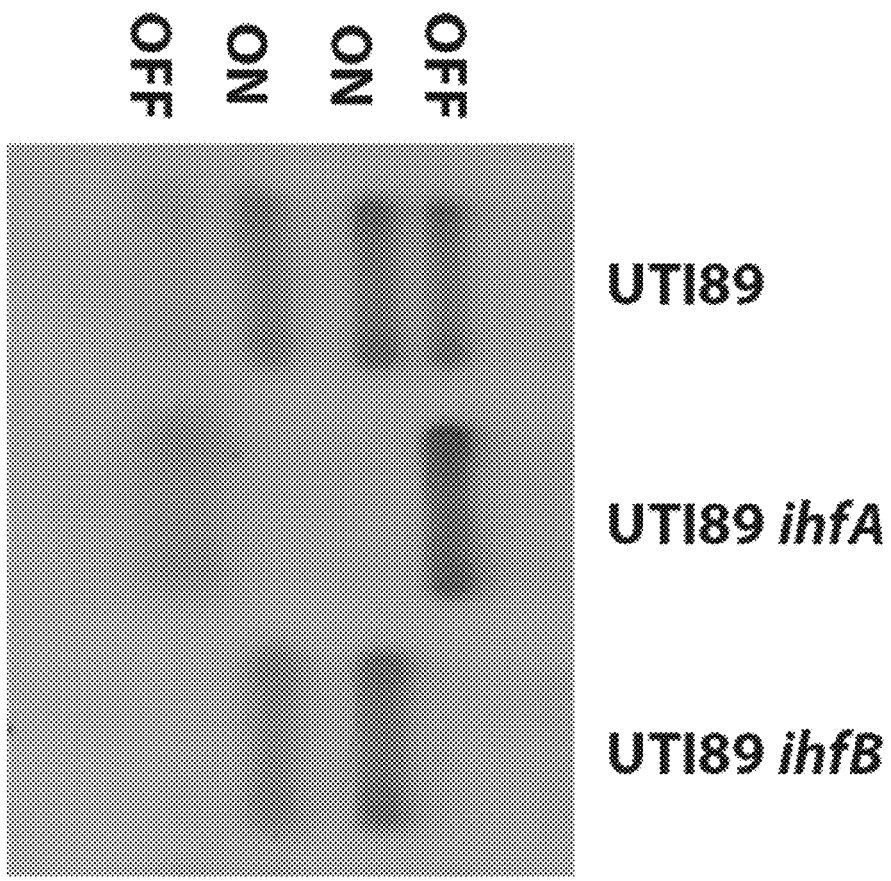
FIG. 1 shows the promoter orientation. The promoter region (fimS) from UTI89, ROL745 and ROL603 were amplified by PCR and digested as previously described (Smith, S. G. et al. (1999) Mol. Microbiol. 34:965-979). The size of the fragments following digestion indicates the orientation of the promoter ("off"=539 & 187 bp, while "on"=433 & 293 bp). A representative gel is shown to demonstrate the different orientations observed in the UTI89 wild type and mutant strains. The mutated genes are indicated above each lane.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration and molecular weight, including ranges, are approximations which are varied (+) or (−) by increments of 1.0 or 0.1, as appropriate, or alternatively by a variation of +/−15%, or alternatively 10%, or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention. Embodiments defined by each of these transition terms are within the scope of this invention.

A "DNABII polypeptide or protein" intends a DNA binding protein or polypeptide that is composed of DNA-binding domains and thus have a specific or general affinity for DNA. In one aspect, they bind DNA in the minor grove. Non-limiting examples of DNABII proteins are an integration host factor (IHF) protein and a histone-like protein from *E. coli* strain U93 (HU). Non-limiting examples of IHF and HU bacteria are provide in Table 2, infra.

A "DNABII family member" or a "DNABII bacteria" intends a bacteria that produces a DNABII protein or polypeptide. A non-limiting example is *E. coli* strain U93 (HU).

A "bacteria relevant antibody" intends an antibody (polyclonal, monoclonal or fragment thereof) that recognizes and binds the DNABII protein or polypeptide of the bacteria to which the therapy is intended. For example, a bacteria relevant antibody for IHF protein is an antibody that specifically recognizes and binds IHF from, for example, *E. coli* strain U93.

An "integration host factor" or "IHF" protein is a bacterial protein that is used by bacteriophages to incorporate their DNA into the host bacteria. These are DNA binding proteins that function in genetic recombination as well as in transcription and translational regulation. They also bind extracellular microbial DNA. The genes that encode the IHF protein subunits in *E. coli* are himA (Genbank accession No.: POA6X7.1) and himD (POA6Y1.1) genes.

"HU" or "histone-like protein from *E. coli* strain U93" refers to a class of homodimeric or heterodimeric proteins typically associated with *E. coli*. HU proteins are known to bind DNA Holliday junctions. Related proteins have been isolated from other microorganisms. The complete amino acid sequence of *E. coli* HU was reported by Laine et al. (1980) Eur. J. Biochem. 103(3):447-481.

A "subject" of diagnosis or treatment is a cell or an animal such as a mammal or a human. Non-human animals subject to diagnosis or treatment and are those subject to infections or animal models, for example, simians, murines, such as, rats, mice, chinchilla, canine, such as dogs, leporids, such as rabbits, livestock, sport animals and pets.

The term "protein", "peptide" and "polypeptide" are used interchangeably and in their broadest sense refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

A polynucleotide or polynucleotide region (or a polypeptide or polypeptide region) having a certain percentage (for example, 80%, 85%, 90% or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 30% identity or alternatively less than 25% identity, less than 20% identity, or alternatively less than 10% identity with one of the sequences of the present invention.

"Homology" or "identity" or "similarity" can also refer to two nucleic acid molecules that hybridize under stringent conditions to the reference polynucleotide or its complement.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, the terms "treating," "treatment" and the like are used herein to mean obtaining a desired pharmacologic and/or physiologic effect. The effect may be prophylactic in terms of completely or partially preventing a disorder or sign or symptom thereof and/or may be therapeutic in terms of a partial or complete cure for a disorder and/or adverse effect attributable to the disorder.

To "prevent" intends to prevent a disorder or effect in vitro or in vivo in a system or subject that is predisposed to the disorder or effect, infection with the bacteria or a disorder or condition associated with the infection. Thus, a subject may be infected with a bacteria in one tissue yet be clear of infection in another tissue. To "prevent" infection can therefore encompass infection of the bacterial-free tissue in the subject.

"Pharmaceutically acceptable carriers" refers to any diluents, excipients or carriers that may be used in the compositions of the invention. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like and consistent with conventional pharmaceutical practices.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include oral administration, nasal administration, injection and topical application.

The term "effective amount" refers to a quantity sufficient to achieve a beneficial or desired result or effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in a protective response against a pathogen. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The agents and compositions can be used in the manufacture of medicaments and for the treatment of humans and other animals by administration in accordance with conventional procedures, such as an active ingredient in pharmaceutical compositions.

An agent of the present invention can be administered for therapy by any suitable route of administration. It will also be appreciated that the preferred route will vary with the condition and age of the recipient and the disease being treated.

As used herein, the terms "antibody" "antibodies" and "immunoglobulin" includes whole antibodies and any antigen binding fragment or a single chain thereof. Thus the term "antibody" includes any protein or peptide containing molecule that comprises at least a portion of an immunoglobulin molecule. The terms "antibody," "antibodies" and "immunoglobulin" also include immunoglobulins of any isotype, fragments of antibodies which retain specific binding to antigen, including, but not limited to, Fab, Fab', F(ab)$_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, at least one portion of a binding protein, chimeric antibodies, humanized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues. The term "anti-" when used before a protein name, anti-IHF, anti-HU, for example, refers to a monoclonal or polyclonal antibody or fragment thereof that binds and/or has an affinity to a particular protein. For example, "anti-IHF" refers to an antibody or fragment thereof that binds to the IHF protein. The specific antibody may have affinity or bind to proteins other than the protein it was raised against. For example, anti-IHF, while specifically raised against the IHF protein, may also bind other proteins that are related either through sequence homology or through structure homology.

The antibodies can be polyclonal, monoclonal, multispecific (e.g., bispecific antibodies), and antibody fragments, so long as they exhibit the desired biological activity. Antibodies can be isolated from any suitable biological source, e.g., murine, rat, sheep and canine or recombinantly produced.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

Monoclonal antibodies may be generated using hybridoma techniques or recombinant DNA methods known in the art. A hybridoma is a cell that is produced in the laboratory from the fusion of an antibody-producing lymphocyte and a non-antibody producing cancer cell, usually a myeloma or lymphoma. A hybridoma proliferates and produces a continuous syple of a specific monoclonal antibody. Alternative techniques for generating or selecting antibodies include in vitro exposure of lymphocytes to antigens of interest, and screening of antibody display libraries in cells, phage, or similar systems.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies. Methods to making these antibodies are described herein.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are described herein.

As used herein, chimeric antibodies are antibodies whose light and heavy chain genes have been constructed, typically by genetic engineering, from antibody variable and constant region genes belonging to different species.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin. a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

As used herein, the term "antibody derivative", comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof.

As used herein, the term "label" intends a directly or indirectly detectable compound or composition that is conjugated directly or indirectly to the composition to be detected, e.g., N-terminal histadine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals ($6^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

A "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The terms "antigen" and "antigenic" refer to molecules with the capacity to be recognized by an antibody or otherwise act as a member of an antibody-ligand pair. "Specific binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term "antigenic" is an adjectival reference to molecules having the properties of an antigen. The term encompasses substances which are immunogenic, i.e., immunogens, as well as substances which induce immunological unresponsiveness, or anergy, i.e., anergens.

An "altered antigen" is one having a primary sequence that is different from that of the corresponding wild-type antigen. Altered antigens can be made by synthetic or recombinant methods and include, but are not limited to, antigenic peptides that are differentially modified during or after translation, e.g., by phosphorylation, glycosylation, cross-linking, acylation, proteolytic cleavage, linkage to an antibody molecule, membrane molecule or other ligand. (Ferguson et al. (1988) Ann. Rev. Biochem. 57:285-320). A synthetic or altered antigen of the invention is intended to bind to the same TCR as the natural epitope.

A supporting therapy, as used herein, is a composition or therapy that when used in combination, supports or augments the method or composition of this disclosure. For example, a supporting therapy can be the co-administration of an antibacterial that will work in combination with the methods and compositions of this disclosure.

Modes for Carrying Out the Disclosure

Therapeutic Methods

This disclosure provides methods to inhibit, prevent infection or inhibit or prevent the spread of infection of a bacteria in a cell (or to surrounding tissue) that may infect the cell or tissue (e.g., the bacteria is in tissue in close proximity to the cell to be treated) wherein the bacteria is a DNABII family member or exports a DNABII protein. The method comprises, or alternatively consists essentially of, or yet further consists of administering to a tissue infected with the bacteria an effective amount of an antibody that specifically recognizes and binds the DNABII protein produced by the bacteria, thereby inhibiting or preventing infection of the bacteria. Non-limited examples of such bacteria include *Vibrio vulnificus, Vibrio cholera, E. coli, Legionella pneumophila, Salmonella, Shigella, Listeria, Aggregatibacter* and *Neisseria* For the purpose of the methods, the contacting is in vitro or in vivo and the antibody that is administered is selective for the bacterial infection to be prevented or inhibited. The antibody can be elicited by either active vaccination of the host with proteins of the bacterial specific DNABII family or passive transfer of antiserum or an antibody against a protein or proteins of the DNABII family. The methods can further comprise, or consist essentially of, or yet further consist of, administration of additional antibacterial compositions. One of skill in the art can determine when the infection is inhibited or prevented using methods known in the art, for example, by screening or assaying for the presence of the bacteria in the putative host or culture containing the bacteria.

This disclosure also provides methods to treat a bacterial infection in subject in need thereof, wherein the subject is infected with a DNABII bacteria or a bacteria that exports DNABII protein, the method comprising, or alternatively consisting essentially of, or yet further consisting of, administering to the subject an effective amount of an antibody that specifically recognizes and binds a DNABII protein produced by the bacteria, thereby treating the bacterial infection. Non-limited examples of such bacteria include *Vibrio vulnificus, Vibrio cholera, E. coli, Legionella pneumophila, Salmonella, Shigella, Listeria, Aggregatibacter* and *Neisseria* For the purpose of the methods, the contacting is in vitro or in vivo and the antibody that is administered is selective for the bacterial infection to be treated. The source of antibody against the bacterial specific DNABII family member can be elicited by either active vaccination of the host with proteins of the bacterial specific DNABII family or passive transfer of antiserum or an antibody against proteins of the DNABII family. The methods can further comprise, or consist essentially of, or yet further consist of, administration of additional antibacterial compositions. One of skill in the art can determine when the infection is treated using methods known in the art, for example, by screening or assaying for the presence of the bacteria in the putative host or culture containing the bacteria.

Yet further provides are methods to treat a condition in a subject in need thereof, wherein the condition is associated with a bacterial infection wherein the bacteria is DNABII family member or exports a DNABII protein, the method comprising, or alternatively consisting essentially of, or yet further consisting of, administering to the subject an effective amount of an antibody that specifically recognizes and binds a DNABII protein produced by the bacteria, thereby treating the condition in the subject. A non-limiting example of a condition is cystitis. Non-limiting examples of bacteria that can produce conditions are provided above and incorporated by reference herein, e.g., *Vibrio vulnificus, Vibrio cholera, E. coli, Legionella pneumophila, Salmonella, Shigella, Listeria, Aggregatibacter* and *Neisseria* For the purpose of the methods, the antibody that is administered is selective for the bacterial infection associated with the condition. The antibody can be elicited by either active vaccination of the host with proteins of the DNABII family or passive transfer of antiserum or an antibody against proteins of the DNABII family. One of skill in the art can determine when the condition is treated using methods known in the art, for example, by screening or assaying for the presence of the bacteria in the putative host or culture containing the bacteria.

For the purpose of the above methods, the antibody is one or more of a a polyclonal antibody, a monoclonal antibody, a humanized antibody, a human antibody, an antibody derivative, a veneered antibody, a diabody, an antibody derivative, a recombinant human antibody, a chimeric antibody, or an antibody fragment, e.g., a single-chain antibody. In one aspect, administration is local to the site of infection. In one aspect, the effective amount or contacting of the antibody is achieved by coating or incorporation of the antibody on a in situ device or microcapsule, such as a micelle or liposome. For example, the antibody can be coated or attached to a catheter.

Also provided are compositions comprising, or alternatively consisting essentially of, or yet further consisting of, an effective amount of an antibody that specifically recognizes and binds a DNABII protein, in an amount to prevent infection of a cell by a bacteria that exports DNABII protein and a carrier. The antibody in the composition is one or more of a polyclonal antibody, a monoclonal antibody, a humanized antibody, a human antibody, an antibody derivative, a veneered antibody, a diabody, an antibody derivative, a recombinant human antibody, a chimeric antibody, or an antibody fragment, e.g., a single chain antibody. In one aspect, the carrier is a pharmaceutically acceptable carrier.

A "composition" typically intends a combination of the active agent and another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-, oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional proviso that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", 52$^{nd}$ ed., Medical Economics, Montvale, N.J. (1998).

The invention provides an article of manufacture, comprising packaging material and at least one vial comprising a solution of the chemotherapy as described herein and/or or at least one antibody or its biological equivalent with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising the chemotherapy and/or at least one lyophilized antibody or its biological equivalent and a second vial comprising an aqueous diluent of prescribed buffer or preservative, wherein said packaging material comprises a label that instructs a patient to reconstitute the therapeutic in the aqueous diluent to form a solution that can be held over a period of twenty-four hours or greater.

The agents identified herein as effective for their intended purpose can be administered to subjects or individuals identified by the methods herein as suitable for the therapy. Therapeutic amounts can be empirically determined and will vary with the pathology being treated, the subject being treated and the efficacy and toxicity of the agent.

In various embodiments of the methods of the invention, the active will be administered locally or systemically on a continuous, daily basis, at least once per day (QD) and in various embodiments two (BID), three (TID) or even four times a day. Typically, the therapeutically effective daily dose will be at least about 1 mg, or at least about 10 mg, or at least about 100 mg or about 200-about 500 mg and sometimes, depending on the compound, up to as much as about 1 g to about 2.5 g.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

In one aspect, the antibodies, fragments and derivatives thereof are formulated in biodegradable biospheres (e.g., micelles or liposomes) or are coated on solid phase carriers such as or other devices.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

Combination Therapy

The compositions and related methods of the present invention may be used in combination with the administration of other therapies. These include, but are not limited to, the administration of antibiotics, antimicrobials, or other antibodies.

In other embodiments, the methods and compositions can be combined with antibiotics and/or antimicrobials. Antimicrobials are substances that kill or inhibit the growth of microorganisms such as bacteria, fungi, or protozoans. In other embodiments, the use of antibiotics or antimicrobials in combination with methods and compositions described herein allow for the reduction of the effective amount of the antimicrobial and/or antibacterial. Some non-limiting examples of antimicrobials and antibiotics useful in combination with methods of the current invention include amoxicillin, amoxicillin-clavulanate, cefdinir, azithromycin, and sulfamethoxazole-trimethoprim. The therapeutically effective dose of the antimicrobial and/or antibiotic in combination with agent can be readily determined by traditional methods. In some embodiments the dose of the antimicrobial agent in combination with the antibody is the average effective dose which has been shown to be effective in other bacterial infections. In other embodiments, the dose is 0.1, 0.15, 0.2, 0.25, 0.30, 0.35, 0.40, 0.45, 0.50, 0.55, 0.60, 0.65, 0.70, 0.75, 0.8, 0.85, 0.9, 0.95, 1.1, 1.2, 1.3, 1.4, 1.5, 1.6, 1.7, 1.8, 1.9, 2.0, 2.5, 3.0 or 5 times the average effective dose. The antibiotic or antimicrobial can be added prior to, concurrent with, or subsequent to the addition of the anti-DNABII antibody.

The additional therapeutic treatment can be added prior to, concurrent with, or subsequent to methods or compositions used to prevent or treat bacterial infections and associated conditions, and can be contained within the same formulation or as a separate formulation.

Screening Assays

The present invention provides methods for screening for equivalent agents, such as small, molecules, peptides, equivalent monoclonal antibodies to a polyclonal antibody as described herein and various agents that modulate the activity of the active agents and pharmaceutical compositions of the invention. For the purposes of this invention, an "agent" is intended to include, but not be limited to a biological or chemical compound such as a simple or complex organic or inorganic molecule, a peptide, a protein (e.g. antibody), a polynucleotide (e.g. anti-sense) or a ribozyme. A vast array of compounds are available in pre-synthesized libraries or can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen.

To perform an in vitro screen one of skill in the art can modify the methods provided infra. For example, cultures of the bacteria are prepared, e.g., by culturing overnight and then diluting to the appropriate concentration, e.g., about $1 \times 10^5$ CFU/ml in minimal essential medium (ATCC; Manassas, Va.) or other appropriate medium. In one embodiment, at least two identical cultures are prepared, one for the candidate agent and the other to be a control for comparison of activity. In one aspect, various dilutions of antibody and agent are contacted with separate cultures for comparison. In one aspect, the medium is overlayed onto a confluent monolayer of HTB-4 human bladder transitional carcinoma cells (ATCC; Manassas, Va.). Binding can be facilitated by centrifugation before cells were washed, lysed and bound then the bacteria were enumerated as known in the art, e.g. Justice et al., 2006b. An agent is a potential therapeutic if the antibody binds to the protein. In aspect, the binding is compared to the binding activity of a control antibody. In one aspect, the agent is a potential therapeutic if the activity is at least 70%, or alternatively, at least 75%, or alternatively, at least 80%, or alternatively, at least 85%, or alternatively, at least 90%, or alternatively, at least 95%, or alternatively, greater than that of the control antibody.

In another embodiment, the candidate agent can be tested in vivo by administration to an appropriate animal model, as discussed infra. An agent is a potential therapeutic if infection is inhibited or prevented. In one aspect, the degree of infection is compared to a control antibody, and is a potential therapeutic if the activity is at least 70%, or alternatively, at least 75%, or alternatively, at least 80%, or alternatively, at least 85%, or alternatively, at least 90%, or alternatively, at least 95%, or alternatively, greater than that of the control antibody.

Kits

Kits containing the agents and instructions necessary to perform the in vitro and in vivo methods as described herein also are claimed. Accordingly, the invention provides kits for performing these methods which may include antibody of this invention as well as instructions for carrying out the methods of this invention such as collecting tissue and/or performing the screen and/or analyzing the results and/or administration of an effective amount of antibody or other agent as defined herein. These can be used alone or in combination with other suitable antimicrobial agents.

General Methods for Antibody Production

Antibody Compositions

The disclosure, in another aspect, provides an antibody that binds to a member of the DNABII family of proteins. The antibody can be a polyclonal antibody, a monoclonal antibody, a chimeric antibody, a humanized antibody or a derivative or fragment thereof as defined below. In one aspect, the antibody is detectably labeled or further comprises a detectable label conjugated to it.

Also provided is a composition comprising the antibody and a carrier. Further provided is a biologically active fragment of the antibody, or a composition comprising the antibody fragment. Suitable carriers are known in the art, some of which are provided herein.

Further provided is an antibody-peptide complex comprising, or alternatively consisting essentially of, or yet alternatively consisting of, the antibody and DNABII protein specifically bound to the antibody.

This disclosure also provides an antibody capable of specifically forming a complex with a DNABII protein, which are useful in the therapeutic methods of this disclosure. The term "antibody" includes polyclonal antibodies and monoclonal antibodies, antibody fragments, as well as derivatives thereof (described above). The antibodies include, but are not limited to mouse, rat, and rabbit or human antibodies. Antibodies can be produced in cell culture, in phage, or in various animals, including but not limited to cows, rabbits, goats, mice, rats, hamsters, guinea pigs, sheep, dogs, cats, monkeys, chimpanzees, apes, etc. The antibodies are also useful to identify and purify therapeutic polypeptides.

This disclosure also provides an antibody-peptide complex comprising, or alternatively consisting essentially of, or yet alternatively consisting of, antibodies described above and a polypeptide specifically bound to the antibody. In one aspect the polypeptide is the polypeptide against which the antibody was raised. In one aspect the antibody-peptide complex is an isolated complex. In a further aspect, the antibody of the complex is, but not limited to, a polyclonal antibody, a monoclonal antibody, a humanized antibody or an antibody derivative described herein. Either or both of the antibody or peptide of the antibody-peptide complex can be detectably labeled or further comprises a detectable label conjugated to it. In one aspect, the antibody-peptide complex of the disclosure can be used as a control or reference sample in diagnostic or screening assays.

Polyclonal antibodies of the disclosure can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, which induces the B-lymphocytes to produce IgG immunoglobulins specific for the antigen. This IgG is purified from the mammals serum. Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antiben depot, which allows for a slow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods described in U.S. Pat. Nos. 7,279,559; 7,119,179; 7,060,800; 6,709,659; 6,656,746; 6,322,788; 5,686,073; and 5,670,153.

The monoclonal antibodies of the disclosure can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived therefrom, or any other suitable cell line as known in the art (see, e.g., www.atcc.org, www.lifetech.com., last accessed on Nov. 26, 2007, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods.

In one embodiment, the antibodies described herein can be generated using a Multiple Antigenic Peptide (MAP) system. The MAP system utilizes a peptidyl core of three or seven radially branched lysine residues, on to which the antigen peptides of interest can be built using standard solid-phase chemistry. The lysine core yields the MAP bearing about 4 to 8 copies of the peptide epitope depending on the inner core that generally accounts for less than 10% of total molecular weight. The MAP system does not require a carrier protein for conjugation. The high molar ratio and dense packing of multiple copies of the antigenic epitope in a MAP has been shown to produce strong immunogenic response. This method is described in U.S. Pat. No. 5,229,490 and is herein incorporated by reference in its entirety.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsreid/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) Microbiol. Immunol. 41:901-907; Sandhu et al. (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al. (1196) Proc. Natl. Acad. Sci. USA 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134.

Antibody derivatives of the present disclosure can also be prepared by delivering a polynucleotide encoding an antibody of this disclosure to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

Antibody derivatives also can be prepared by delivering a protein or polynucleotide to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbiol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present disclosure can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies of the present disclosure can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 68(4):1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Delivery Reviews 31:33-42; Green & Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417): 255-258; Jakobovits et al. (1993) Proc. Natl. Acad. Sci. USA 90(6):2551-2555; and U.S. Pat. No. 6,075,181).

The antibodies of this disclosure also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies of this disclosure can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological Interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448). By using a linker that is too short to allow pairing between the two domains on the same chain, the domains are forced to pair with the complementary domains of another chain and create two antigen-binding sites. (See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen).

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Fd segments ($V_H$-$C_H1$-VH-$C_H1$) which form a pair of antigen binding regions. Linear antibodies can be bispecific or monospecific.

The antibodies of this disclosure can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present disclosure include naturally purified products, products of chemical synthetic procedures, and products produced by recombinant techniques from a eukaryotic host, including, for example, yeast, higher plant, insect and mammalian cells, or alternatively from a prokaryotic cells as described above.

If a monoclonal antibody being tested binds with protein or polypeptide, then the antibody being tested and the antibodies provided by the hybridomas of this disclosure are equivalent. It also is possible to determine without undue experimentation, whether an antibody has the same specificity as the monoclonal antibody of this disclosure by determining whether the antibody being tested prevents a monoclonal antibody of this disclosure from binding the protein or polypeptide with which the monoclonal antibody is normally reactive. If the antibody being tested competes with the monoclonal antibody of the disclosure as shown by a decrease in binding by the monoclonal antibody of this disclosure, then it is likely that the two antibodies bind to the same or a closely related epitope. Alternatively, one can pre-incubate the monoclonal antibody of this disclosure with a protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this disclosure.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307.

The isolation of other hybridomas secreting monoclonal antibodies with the specificity of the monoclonal antibodies of the disclosure can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody produced by the hybridoma of interest.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

In some aspects of this disclosure, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow & Lane (1988) supra.

The antibodies of the disclosure also can be bound to many different carriers. Thus, this disclosure also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the disclosure. Those skilled in the art will know of other suitable carriers for binding monoclonal antibodies, or will be able to ascertain such, using routine experimentation.

Experimental Procedures

The DNABII family of proteins is also observed in the bacterial milieu (extrabacterial) (Winters, B. D. et al. (1993) Infect. Immun. 61:3259-3264; Lunsford, R. D. et al. (1996) Curr. Microbiol. 32:95-100; Kim, N. et al. (2002) J. Bacteriol. 184:6155-6162). The extrabacterial accumulation of the *Streptococcus* DNABII family member, HlpA, elicits a proinflammatory immune response in macrophages (Zhang, L. et al. (1999) Infect. Immun. 67:6473-6477) that may contribute to tissue damage associated with infection.

Extrabacterial DNA (eDNA) is a key component of communities formed by many pathogenic bacterial species (Flemming, H. C. et al. (2010) Nature Reviews. Microbiology 8:623-633). The DNABII family is also critical for the integrity of bacterial communities that utilize eDNA within the matrix. It was demonstrated that antibodies directed against *E. coli* DNABII family members disrupt communities formed by multiple human pathogens under laboratory conditions (Goodman, S. D. et al. (2011) Mucosal Immunol. 4:625-637). Sequestration of DNABII family members from the extrabacterial community matrix also increased bacterial sensitivity to antimicrobials (Goodman, S. D. et al. (2011) Mucosal Immunol. 4:625-637). In addition, vaccination against IHF resolved pre-existing otitis media mediated by non-typeable *Haemophilus influenzae* in a mammalian model of human disease (Goodman, S. D. et al. (2011) Mucosal Immunol. 4:625-637). Therefore, extrabacterial DNABII members, specifically IHF, appear to be a plausible target for prevention and/or treatment of community-based infectious diseases.

In this study, the contribution of IHF to the pathogenic lifestyle of UPEC was investigated. The addition of antibodies directed against extrabacterial (eIHF) was observed to reduced the attachment of UPEC to bladder epithelial cells, suggesting eIHF as a potential target for prevention of urinary tract infections (UTIs). Since these antibodies are merely specific for a members of the DNABII family and not specifically for IHF, and the fact that all bacteria tested to date export a member of the DNABII family it can be concluded that the DNABII family is target for interference for host cell interaction a prelude to pathogenesis.

Bacteria Strains and Plasmids

The strains and plasmids used in this study are indicated in Table 1. Constitutive synthesis of green fluorescent protein was performed using pANT4 (previously designated pCOMGFP) (Lee, A. K. et al. (1998) Infect. Immun. 66:3964-3967; Justice, S. S. et al. (2004) Proc. Natl. Acad. Sci. U.S.A. 101:1333-1338). Production of either or both IHF subunits was accomplished using pHNα (Granston, A. E. et al. (1993) J. Mol. Biol. 234:45-59), pHNβ (kindly provided by Howard Nash), or pHNαβ (Lee, E. C. et al. (1992) The EMBO Journal 11:305-313).

TABLE 1

Strains and Type 1 pilus phenotypes. The genotype of the strains and sources are indicated in the table. The orientation of the fimS promoter sequence is indicated. In cases where the promoter orientation was mixed in the culture, the predominant orientation is indicated in parentheses.

| Strain Name | Genotype | Source |
| --- | --- | --- |
| BW25113 | rrnB3 ΔlacZ4787 hsdR514 Δ(araBAD)567 Δ(rhaBAD)568 rph-1 | [62] |
| JW1702-1 | BW25113 ΔihfA786::kan | [62] |
| JW0895-3 | BW25113 ΔihfB735::kan | [62] |
| K1141 | ihfA11::Tn10 | E. coli Stock Center |
| MG1655 | F⁻ lambda⁻ ilvG- rfb-50 rph-1 | [63] |
| N99 | ΔgalK | [64] |
| SG83 | N99 ihfB::Cam | [65] |
| SG84 | N99 ihfAΔ82 Tn10 | [66] |
| SJ1000 | UTI89 surA:kan | [67] |
| UTI89 ΔkpsF | Polar inactivation of region I | [40] |
| ROL607 | MG1665 ihfB::Cam ihfA11::Tn10 | This study |
| UTI89 | Cystitis Clinical Isolate | [8] |
| | UTI89/pANT4 | [2] |
| ROL745 | UTI89 ihfA11::Tn10 | This study |
| | UTI89 ihfA11::Tn10/pHNα | This study |
| | UTI89 ihfA11::Tn10/pHNβ | This study |
| ROL747 | UTI89 ΔihfA786::kan | This study |
| | UTI89 ΔihfA786:::kan/pHNα | This study |
| | UTI89 ΔihfA786:::kan/pHNβ | This study |
| ROL603 | UTI89 ihfB::Cam | This study |
| | UTI89 ihfB::Cam/pHNα | This study |
| | UTI89 ihfB::Cam/pHNβ | This study |
| ROL748 | UTI89 ΔihfB735::kan | This study |
| | UTI89 ΔihfB735::kan/pHNα | This study |
| | UTI89 ΔihfB735::kan/pHNβ | This study |

Media and Growth

Bacteria were grown 37° C. in Luria-Bertani (LB; Fisher Scientific, Pittsburgh, Pa.) broth in the absence of aeration unless otherwise indicated (planktonic). For assessment of community development in vitro, E. coli strains indicated were prepared as described (Goodman, S. D. et al. (2011) Mucosal Immunol. 4:625-637). When appropriate, antibiotics were used at the following concentrations: 30 μg/ml kanamycin, 25 μg/ml chloramphenicol, 25 μg/ml tetracycline hydrochloride, or 100 μg/ml ampicillin (Fisher Scientific, Pittsburgh, Pa.).

The fimS Orientation

Twenty-five microliters of overnight liquid cultures as well as in vitro community cultures (Goodman, S. D. et al. (2011) Mucosal Immunol. 4:625-637) of various growth phases of planktonic and biofilms were lysed, and the supernatants containing chromosomal DNA were used for amplification of the fimS region. The amplification products were digested with BstUI (New England Biolabs) and visualized following separation on a 2% agarose gel as described previously (Smith, S. G. et al. (1999) Mol. Microbiol. 34:965-979) to determine the orientation ("off"=539 & 187 bp, while "on"=433 & 293 bp) of the promoter.

Inactivation of ihfA and ihfB in MG1655 & UTI89

Laboratory strains of E. coli that carry the individual mutations were obtained from various sources (Table 1). The mutations were introduced into the prototypical UPEC strain, UTI89, and a laboratory adapted strain, MG1655, from the laboratory strains by P1 transduction (Silha, T. J. et al. (1984) Cold Spring Harbor Laboratory:111-113). To facilitate P1 binding to UPEC, cultures were grown at room temperature to reduce production of the K1 capsule (Bortolussi, R. et al. (1983) Infect. Immun. 39:1136-1141).

In Vitro Yeast Agglutination Assay

The mannose-sensitive Yeast Agglutination (YA) assay to determine the extent of type 1 piliation was performed as previously described (Li, B. et al. (2010) Microbes Infect. 12:662-668).

Mouse Infections

UTI89, ROL745 (UTI89 ihfA11::Tn10) and ROL603 (UTI89 ΔihfB) were grown in LB broth in the absence of aeration for 16 hours to an $OD_{600}$~1.2 at 37° C. Inoculum of each strain was normalized such that ~$10^7$ bacteria were transurethrally introduced directly to the bladders of female C3H/HeNHsd mice (Harlan Sprague Laboratory; Indianapolis, Ind.) as previously described (Mulvey, M. A. et al. (1998) Science 282:1494-1497; Justice, S. S. et al. (2004) Proc. Natl. Acad. Sci. U.S.A. 101:1333-1338; Hung, C. S. et al. (2009) Nat. Protoc. 4:1230-1243). Tissues were harvested at times indicated post-inoculation. Statistical significance was determined using a two-tailed Mann Whitney test of the wild type UTI89 for the comparison with each UPEC mutant individually. The experiments were performed in cohorts of 5 mice and repeated on separate occasions. All data points are presented. All mouse experiments were performed under accredited conditions using Institutional Animal Care and Use Committee-approved protocols (Federal Assurance Number: FWA00002860).

Visualization of Intracellular UPEC

Enumeration of bacterial burden and visualization of UPEC colonization was performed as previously described (Justice, S. S. et al. (2006) Proc. Natl. Acad. Sci. U.S.A. 103:19884-19889; Justice, S. S. et al. (2006) Infect. Immun. 74:4793-4800). Bacterial and host DNA was visualized by the addition of Hoechst 34580 (Invitrogen; Carlsbad, Calif.) for 10 minutes. For visualization of eIHF, fixed bladders were subjected to 0.01% Triton X-100 in PBS for 1 hour to permeabilize the epithelial plasma membranes. Antisera raised against IHF (Cranston, A. E. et al. (1993) J. Mol. Biol. 234:45-59) was diluted 1:100 in PBS and applied to mounted bladder tissues for 1 hour. The presence of specific antibody was visualized using Alexa 594-conjugated anti-IgG reagent (Invitrogen, Carlsbad, Calif.). Bladders were mounted with ProLong Gold antifade reagent (Invitrogen, Carlsbad, Calif.). Images were acquired using an Axiovert 200M inverted epifluorescence microscope equipped with a motorized stage, an Axiocam MRM CCD camera and the Apotome component to improve fluorescence resolution (Carl Zeiss, INC, Thornwood, N.Y.). The levels of the fluorescent images were adjusted to all pixels within the image using Adobe Photoshop (Adobe Systems Incorporated; San Jose, Calif.). Quantitation of bacterial morphologies was performed using Image J (developed at the National Institutes of Health, available at the web sit: rsbweb.nih.gov/ij/) and ProkaryMetrics (Dabdoub, S. et al. (2012) Visual Analytics in Healthcare (in press)).

Binding to Bladder Epithelium in the Presence or Absence of Antisera Directed Against IhfAB Overnight cultures of UTI89, ROL745 (UTI89 ihfA11::Tn10) and ROL603 (UTI89 ΔihfB) were diluted to ~$1 \times 10^5$ CFU/ml in minimal essential medium (ATCC; Manassas, Va.). A 1:50 dilution of antiserum raised against IhfAB (Granston, A. E. et al. (1993) J. Mol. Biol. 234:45-59) was added to the culture for 5 minutes. The medium was then overlayed onto a confluent monolayer of HTB-4 human bladder transitional carcinoma cells (ATCC; Manassas, Va.). Binding was facilitated by centrifugation before cells were washed, lysed and bound then the bacteria were enumerated as previously described (Granston, A. E. et al. (1993) J. Mol. Biol. 234:45-59).

Discussion

IhfB but not IhfA Subunits Support Type 1 Piliation

It has been reported that IHF (referred to as IhfAB) functions in the community matrix of a number of organisms including UPEC (Goodman, S. D. et al. (2011) Mucosal Immunol. 4:625-637) but the role of IhfAB during bacterial cystitis was not reported. IhfAB consists of 2 homologous subunits that form a heterodimer. In contrast to being able to make null alleles in both subunits of the laboratory *E. coli* strain MG1655, Applicants were unable to stably inactivate both subunits within UTI89 except in one combination (Table 1). The introduction of both ihfA11::Tn10 and ΔihfB735::kan into UTI89 resulted in a viable strain (ROL750) that exhibited reduced growth rate as well as diminished maximal optical density. This strain appears crippled and cannot be maintained for extended periods of time in frozen glycerol. Therefore, this strain was not extensively used in this work. There were no significant differences in the growth rates of the remainder of the strains used in this study (data not shown).

Previous studies have demonstrated that IhfAB participates in recombination events associated with promoter orientation of the fim operon (encoding type 1 pilus) in laboratory strains (Corcoran, C. P. et al. (2009) Mol. Microbiol. 74:1071-1082). The type 1 pilus is essential for both bladder colonization and internalization (Hultgren, S. J. et al. (1985) Infect. Immun. 50:370-377; Wright, K. J. et al. (2007) Cell Microbiol. 9:2230-2241; Justice, S. S. et al. (2006) Infect. Immun. 74:4793-4800; Snyder, J. A. et al. (2006) Infect. Immun. 74:1387-1393; Bahrani-Mougeot, F. K. et al. (2002) Mol. Microbiol. 45:1079-1093; Martinez, J. J. et al. (2000) The EMBO Journal 19:2803-2812). Therefore, Applicants next carefully examined the type 1 piliation phenotype of either ihfA or ihfB inactivation in our prototypical cystitis UPEC strain, UTI89. Applicants examined each of the ihf mutations currently available (Table 1) to validate that the observed phenotypes were not allele specific. Type 1 piliation in UPEC strains defective in one or both subunits of IHF was determined using in vitro yeast agglutination assays. The ability of the bacteria to cross-link the yeast cells resulting in yeast cell aggregation is mediated by the type 1 pilus binding to the mannosylated proteins on the yeast surface. Type 1-dependent yeast agglutination was not observed in any of the ihfB mutants (Table 1). Yeast agglutination was restored by the addition of ihfB (pHNβ) or ihfAB (pHNβα) in trans (Table 1). The overproduction of IhfA (pHNα) did not restore agglutination to the ihfB mutant, suggesting that increased protein concentration of the other homologous subunit is not sufficient to compensate for the absence of IhfB. In contrast, mannose sensitive yeast agglutination was observed in the absence of IhfA (Table 1). This observation was confirmed using multiple alleles of ihfA (Table 1) to validate that the observation was not specific for any given allele. In fact, Applicants did observe allele specific differences with regards to piliation (Table 1). Other published reports identified the critical role of IhfAB in type 1 pilus regulation by inactivation of the IhfAB binding sites upstream of fimS (Corcoran, C. P. et al. (2009) Mol. Microbiol. 74:1071-1082), simultaneous inactivation of both ihfA and ihfB (Eisenstein, B. I. et al. (1987) Proc. Natl. Acad. Sci. U.S.A. 84:6506-6510), or using fimS DNA fragments and purified proteins in vitro (Werner, M. H. et al. (1994) Current Biology: CB 4:477-487; Zulianello, L. et al. (1994) The EMBO Journal 13:1534-1540). Under laboratory conditions, inactivation of either IHF subunit typically results in phenotypes that are indistinguishable from the phenotype of bacteria lacking both subunits (Werner, M. H. et al. (1994) Current Biology: CB 4:477-487; Zulianello, L. et al. (1994) The EMBO Journal 13:1534-1540). However, individual subunits readily form functional homodimers in complex with DNA in vitro (Werner, M. H. et al. (1994) Current Biology: CB 4:477-487; Zulianello, L. et al. (1994) The EMBO Journal 13:1534-1540), suggesting that homodimers may form upon stoichiometric changes in levels of the individual subunits. Investigation of a single IHF subunit using an otherwise intact system clearly demonstrates that the IhfB subunit alone is sufficient to function in the absence of the canonical IhfAB heterodimer with regards to the regulation of the type 1 pilus.

Promoter Orientation in the Absence of IHF Subunits

In light of Applicants' observations that the two subunits contribute differently to the regulation of type 1 piliation, Applicants evaluated the phase variation of the promoter region of the fim operon in each of the mutants as previously described (Smith, S. G. et al. (1999) Mol. Microbiol. 34:965-979). IhfAB binding sites are required for phase "on" bias (Eisenstein, B. I. et al. (1987) Proc. Natl. Acad. Sci. U.S.A. 84:6506-6510; Corcoran, C. P. et al. (2009) Mol. Microbiol. 74:1071-1082) of the fim operon encoding the type 1 pilus (Klemm, P. et al. (1985) Molecular & General Genetics: MGG 199:410-414). In the case of UTI89, the culture appears heterogeneous with regards to the orientation of the promoter, as there is an equal distribution of promoters in the "off" and "on" orientation (FIG. 1). In general, the promoter orientation was consistent with the mannose sensitive agglutination results (Table 1, FIG. 1). In contrast to UTI89, the promoter orientation appears fixed in either the "on" or "off" orientation (FIG. 1, Table 1) in the presence of certain alleles. The frequency of "on" orientation in the absence of IhfA was generally low, which is consistent with the frequency of piliation observed by yeast agglutination. In contrast, the promoter was generally observed in the "on" orientation with higher frequency in the absence of IhfB in the pathogenic strain (UTI89) but not the laboratory adapted strain (MG1655; Table 1), suggesting that additional regulatory components may be absent in the laboratory adapted strain. The orientation of the promoter is consistent with previous reports that IhfA alone can support recombination events in a reconstituted system (Werner, M. H. et al. (1994) Current Biology: CB 4:477-487; Zulianello, L. et al. (1994) The EMBO Journal 13:1534-1540). Previous studies have demonstrated that homodimers of the IhfA or IhfB subunit are readily formed in vitro and are capable of binding to the native binding sites that share the consensus sequence SEQ ID NO:1 WATCAANNNNTTR (where W is A or T, N is any nucleotide and R is a purine) albeit with lower specificity and affinity than the heterodimer (Werner, M. H. et al. (1994) Current Biology: CB 4:477-487; Zulianello, L. et al. (1994) The EMBO Journal 13:1534-1540). Consistent with this observation, in Applicants' experimental system, it was discovered that certain IhfAB activities remain when only one of the subunits is inactivated. The absence of detectable piliation in the presence of the "on" orientation of the promoter (in the absence of IhfB) suggests that there may be as yet undefined roles for IhfAB in the production of the type 1 pilus in addition to FimB recombinase-mediated promoter switching (Klemm, P. (1986) The EMBO Journal 5:1389-1393; Corcoran, C. P. et al. (2009) Mol. Microbiol. 74:1071-1082).

Both IhfA and IhfB are Required for Colonization of the Urinary Bladder

Figure 2:
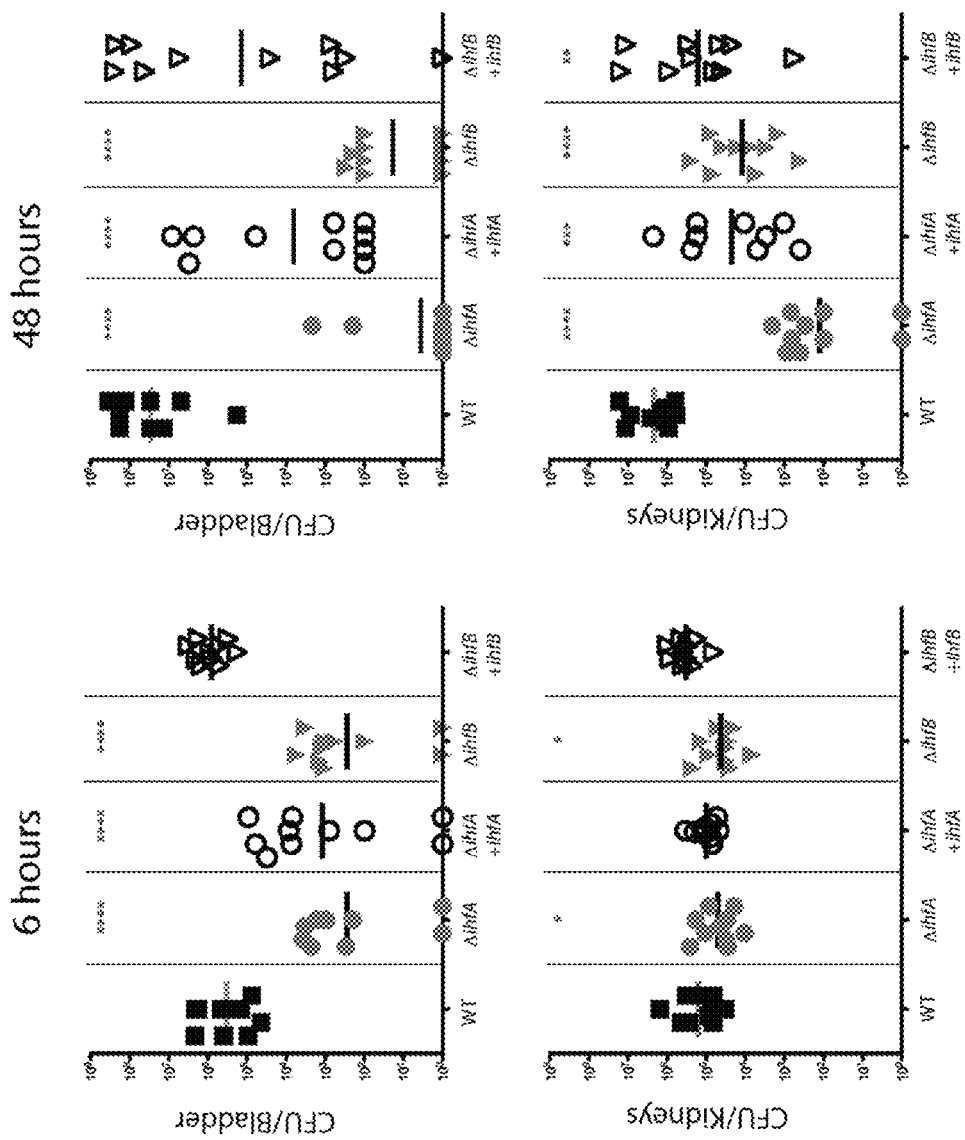
FIG. 2 shows that IhfAB subunits are required for UPEC pathogenesis. Each symbol represents single infected murine bladder or combined kidney pair. Female mice were infected with wild type UTI89 (black filled squares), ROL745 (UTI89 ihfA11; gray filled circles), ROL745/pHNα (UTI89 ihfA11 complemented with ihfA; black open circles), ROL603 (UTI89 ΔihfB; gray filled triangles), or ROL603/pHNβ (UTI89 ihfB::Cam complemented with ihfB; black open triangles) for 6 or 48 hours post inoculation. Bacterial burden of bladders was enumerated as colony forming units (CFUs). Statistical significance determined using non-parametric Mann Whitney (*<0.04, =0.018, *=0.0017, ****<0.0006).

It was previously demonstrated that eIhfAB contributes to the stability of UPEC communities grown on glass surfaces in vitro (Goodman, S. D. et al. (2011) Mucosal Immunol. 4:625-637). Applicants next investigated the contribution of the individual subunits to the intracellular community development observed during cystitis (Justice, S. S. et al. (2004) Proc. Natl. Acad. Sci. U.S.A. 101:1333-1338). Female mice were transurethrally inoculated with UTI89, UTI89 ihfA11::Tn10 (ROL745), UTI89 ΔihfB (ROL603) or the complemented mutant strains to determine the ability of each strain to persist in the urinary tract. Both IhfA and IhfB subunits appear to be required for effective colonization of the bladder as early as 6 hours post infection (FIG. 2). The attenuation is more severe in the bladder at 48 hours post infection, as evidenced by at least a 5 order of magnitude decrease in bacterial burden (p<0.0006). The presence of IhfA alone appears to improve UPEC persistence than the presence of IhfB alone at 48 hours (FIG. 2). The defect in colonization was either partially (IhfA) or fully (IhfB) restored by the presence of the gene of interest in trans (FIG. 2).

Although not directly tested, Applicants assumed that homodimer species is formed in the intact organism, particularly when only one subunit is produced. Given this assumption, this data suggests that there may be independent functions for the homodimers under specific environmental conditions. For example, ihfA expression follows LexA-dependent activation by the SOS response (Miller, H. I. et al. (1981) Proc. Natl. Acad. Sci. U.S.A. 78:6754-6758). Applicants demonstrated that the SOS response is activated in intracellular UPEC during bacterial cystitis (Justice, S. S. et al. (2006) Proc. Natl. Acad. Sci. U.S.A. 103:19884-19889; Li, B. et al. (2010) Microbes Infect. 12:662-668), and Applicants expected that increased production of IhfA in the presence of host immune responses that include DNA damaging agents (i.e. reactive oxygen and nitrogen species) during infection. This increased production of IhfA could result in the presence of both IhfAB heterodimers and IhfA homodimers within the same bacterium during infection. The potential upregulation of IhfA during the SOS response may partially explain the decreased persistence of UTI89 ihfA11::Tn10 during cystitis. As we have demonstrated that individual subunits retain novel properties with regards to community development, it is possible that mixed dimer populations may provide unique roles during the pathogenic lifestyle.

IhfA and IhfB are Dispensable for Early Colonization of the Kidney

In contrast to the bladder, where the IhfA and IhfB subunits are required for early stages of colonization, the absence of either the IhfA or IhfB subunit results in a statistically significant difference (p<0.04) for the colonization of the kidney at 6 hours post infection (FIG. 2). However, the biological relevance for a less than half a log difference at this time point is unclear. The initial slight differences in colonization of the kidney may be indicative of the decline in persistence observed in the kidney through time as seen with the marked decrease in colonization of the kidney with both mutant strains at 48 hours post infection (FIG. 2; p<0.0006). As observed in the bladder tissue, addition of the gene in trans partially complements the phenotype (FIG. 2). The absence of either subunit was better tolerated in the kidney at 48 hours while in comparison the mutants were essentially cleared from the bladder. IhfA alone promotes better colonization of the kidney than IhfB alone, suggesting that the subunits can at least function in the absence of the heterodimer in the kidney. In contrast to UTI89, neither mutant strain demonstrated agglutination to yeast cells following growth on tryptic soy agar (data not shown), suggesting that the P-pilus (important for colonization of the kidney) also requires IhfAB. Thus, as observed with type 1 piliation, there are no differences in production of known adhesins to account for the colonization differences in the kidney.

Proper Community Architecture Requires IhfB During Cystitis

Microscopic evaluation of community development revealed important populations that are essential for UPEC persistence (Justice, S. S. et al. (2004) Proc. Natl. Acad. Sci. U.S.A. 101:1333-1338; Justice, S. S. et al. (2006) Proc. Natl. Acad. Sci. U.S.A. 103:19884-19889; Horvath, D. J., Jr. et al. (2011) Microbes Infect. 13:426-437) in the bladder. Furthermore, the use of UPEC strains defective in specific bacterial traits results in variations in development (Hunstad, D. A. et al. (2010) Annu Rev. Microbiol. 64:203-221). However, the regulatory mechanisms that control UPEC development are not understood. To gain more insight into the potential mechanisms that underlie the persistence defect in the absence of either IhfA or IhfB, we visualized the intracellular bacteria by fluorescence microscopy. Communities were evaluated at 6 hours post infection, when the transition from the rod to coccoid shape generally occurs (Justice, S. S. et al. (2004) Proc. Natl. Acad. Sci. U.S.A. 101:1333-1338; Justice, S. S. et al. (2006) Proc. Natl. Acad. Sci. U.S.A. 103:19884-19889; Justice, S. S. et al. (2006) Infect. Immun. 74:4793-4800). In contrast to the potential for 100s of communities formed with the parental strain, only a few epithelial cells (<2) were infected in the absence of either IhfA or IhfB (data not shown). The lack of visible clusters of bacteria within the epithelial cells indicates that the growth of an organized community is severely crippled in these strains. This phenotype has been observed with other UPEC mutants that display normal growth rates under laboratory conditions (Justice, S. S. et al. (2006) Infect. Immun. 74:4793-4800; Anderson, G. G. et al. (2011) Infect. Immun. 78:963-975; Li, B. et al. (2010) Microbes Infect. 12:662-668).

Figure 3:
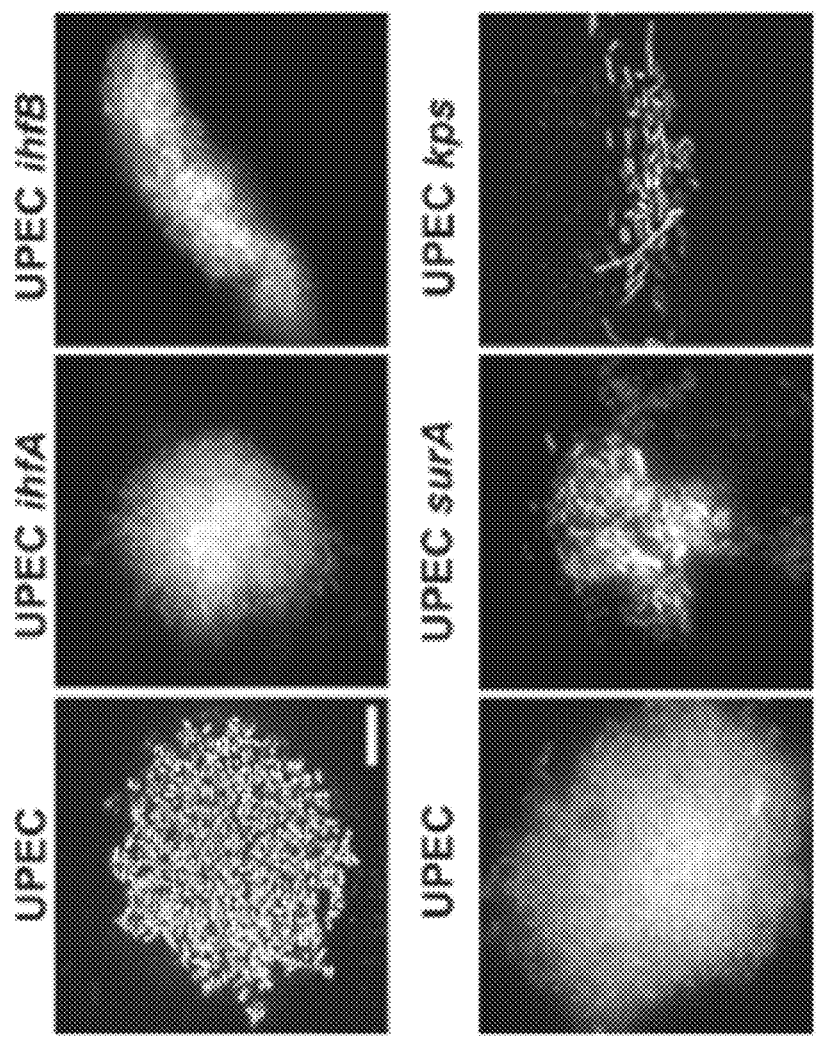
FIG. 3 shows the architecture of Intracellular Bacteria. Female mice were infected with UTI89/pANT4, ROL745/pANT4 (UTI89 ihfA11), or ROL603/pANT4 (UTI89 ΔihfB) for 6 hours. Bladders were prepared for visualization by fluorescent microscopy (Justice, S. S. et al. (2006) Proc. Natl. Acad. Sci. U.S.A. 103:19884-19889). The intracellular characteristics of each of the strains indicated were visualized using strains that constitutively produce green fluorescent protein. Images were taken as an optical section (upper panel UPEC) or as total fluorescence of entire community (all other panels). The strains are indicated above each panel. Scale bar=10 μm.

In the few cases where intracellular clusters were observed, the architecture was aberrant and did not resemble prototypical IBCs (FIG. 3). Consistent with the increase in the bacterial burden, robust IBC development was fully restored by complementation of the gene of interest in trans (data not shown). Although the bacterial burden of the UTI89 ihfA11::Tn10 and UTI89 ΔihfB strains was similar (FIG. 2), there were significant differences in the overall architecture of the IBCs (FIGS. 3 & 4). UTI89 ihfA11::Tn10 retains the ability to form the more globular-shaped IBC as observed with UTI89. In contrast, there is a marked difference in the shape and density of IBCs formed by UTI89 ΔihfB. The differences in the architecture of the intracellular clusters formed in the absence of either subunit further suggests that the individual subunits retain functionality and that, although homologous, are unique.

IhfAB is known to participate in the transcription of type 1 pili and capsule (Rowe, S. et al. (2000) J. Bacteriol. 182:2741-2745; Corcoran, C. P. et al. (2009) Mol. Microbiol. 74:1071-1082). Strains defective in production of the type 1 pilus demonstrate a reduction in the number of infected cells, and in the few cases where intracellular bacteria are detected, there is an absence of interbacterial interactions resulting in evenly distributed bacteria within the cell (Wright, K. J. et al. (2007) Cell Microbiol. 9:2230-2241). Applicants compared the intracellular phenotypes of the IhfA and IhfB mutants with strains deficient in type 1 pili and K1 capsule where aberrant architecture of intracellular clusters was previously described (Justice, S. S. et al. (2006) Infect. Immun. 74:4793-4800; Wright, K. J. et al. (2007) Cell Microbiol. 9:2230-2241; Anderson, G. G. et al. (2011)

Figure 4A:
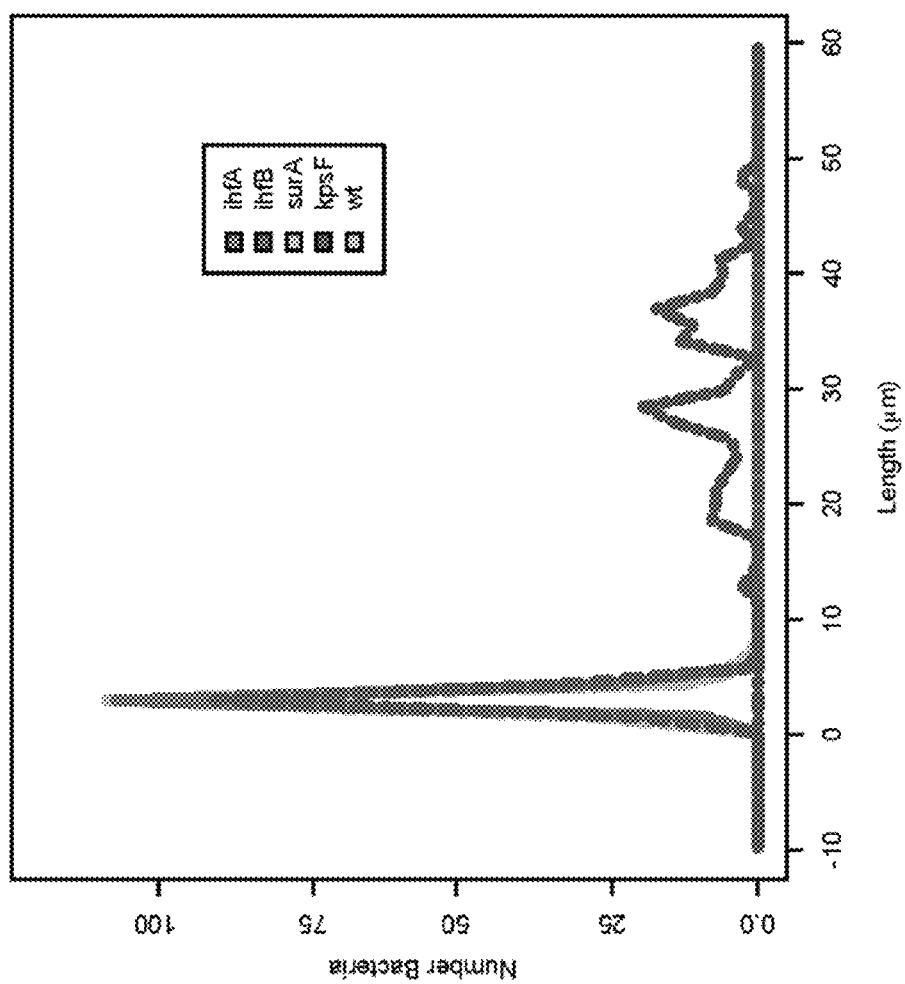

Infect. Immun. 78:963-975). The UTI89 ihfA11::Tn10 retain interbacterial interactions during intracellular growth (FIG. 3) and the more globular architecture of the prototypical IBC, but appear to have reduced growth as compared with the parent (overall area of community) (FIGS. 4A & 4B). Due to the few infected cells observed with the mutant strain, Applicants were unable to determine the contribution of IhfA to the other developmental stages. However, the significant decrease in bacterial burden (FIG. 2) suggests that the later stages of development are also compromised.

The phenotype of the UTI89 ΔihfB included the reduction in the number of intracellular clusters but appears to retain some interbacterial interactions that are unique from other known mutants in IBC architecture (FIG. 3). The interbacterial spacing resembles that of UTI89 surA (defective in type 1 pili and outer membrane beta barrel proteins) (Justice, S. S. et al. (2005) J. Bacteriol. 187:7680-7686; Justice, S. S. et al. (2006) Infect. Immun. 74:4793-4800; Rouviere, P. E. et al. (1996) Genes Dev. 10:3170-3182; Lazar, S. W. et al. (1996) J. Bacteriol. 178:1770-1773) but the overall shape of the cluster is different (FIGS. 4A & 4B). The clusters formed by UTI89 ΔihfB are similar in overall shape with those of the UTI89 kpsF strain (defective in the K1 capsule) (FIGS. 3, 4A & 4B) (Anderson, G. G. et al. (2011) Infect. Immun. 78:963-975). However, unlike the case with UTI89 kpsF, the morphology of the individuals of UTI89 ΔihfB are similar to those produced by the parental strain (FIGS. 4A & 4B), suggesting that the defects in IBC development observed in the absence of IhfB may not be the result of defects in capsule synthesis. Comparison of the architectural and growth characteristics of each UPEC mutant provides addition insight into the specific defects than just evaluation of bacterial burden alone.

IhfAB is Present in Extrabacterial Milieu of IBCs

Figure 5:
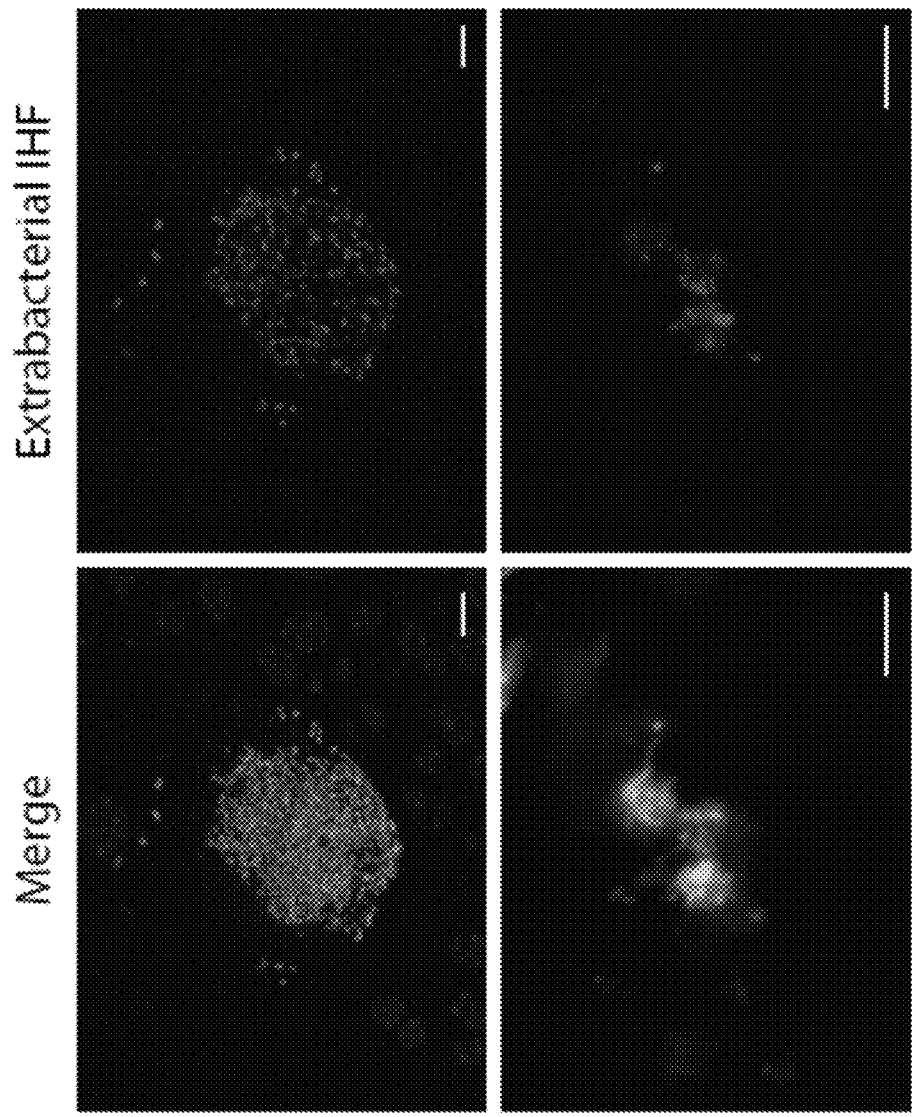
FIG. 5 shows that IhfAB is extrabacterial within the IBC milieu. Bladders were removed at 16 hours following transurethral introduction of UTI89/pANT4. At 16 hours post introduction of bacteria, the bladders were harvested, bisected, fixed, host cells permeabilized and eIhfAB was observed with antibody directed against IhfAB (red) and Hoescht counterstained (blue). Upper panels demonstrate eIhfAB within the epithelial cell. Lower panels demonstrate eIhfAB remains associated with UPEC following egress onto the surface of the bladder. Scale bar=10 μm.

It was previously demonstrated that addition of antibody directed against IhfAB will disrupt the integrity of communities of UPEC grown on glass surfaces (Goodman, S. D. et al. (2011) Mucosal Immunol. 4:625-637), suggesting that eIhfAB is important for the stability of interbacterial interactions. To determine whether IhfAB could be detected in the extrabacterial milieu of IBCs, immunofluorescence microscopy was performed on infected, splayed whole mount mouse bladders. The epithelial cells were permeabilized under conditions that do not affect bacterial cell integrity (Experimental Procedures). Evaluation of IBCs of UTI89 (green) at 16 hours post infection revealed the presence of eIhfAB (red) throughout the community architecture of established IBCs (FIG. 5). In addition, UPEC that egress from infected epithelial cells carry eIhfAB, presumably still attached to the eDNA (FIG. 5). This evidence suggests that IhfAB is a component of the IBC matrix and that some of the phenotypes associated with the aberrant architecture may be associated with defects in the composition or deposition of IhfAB in the IBC matrix.

Figure 6:
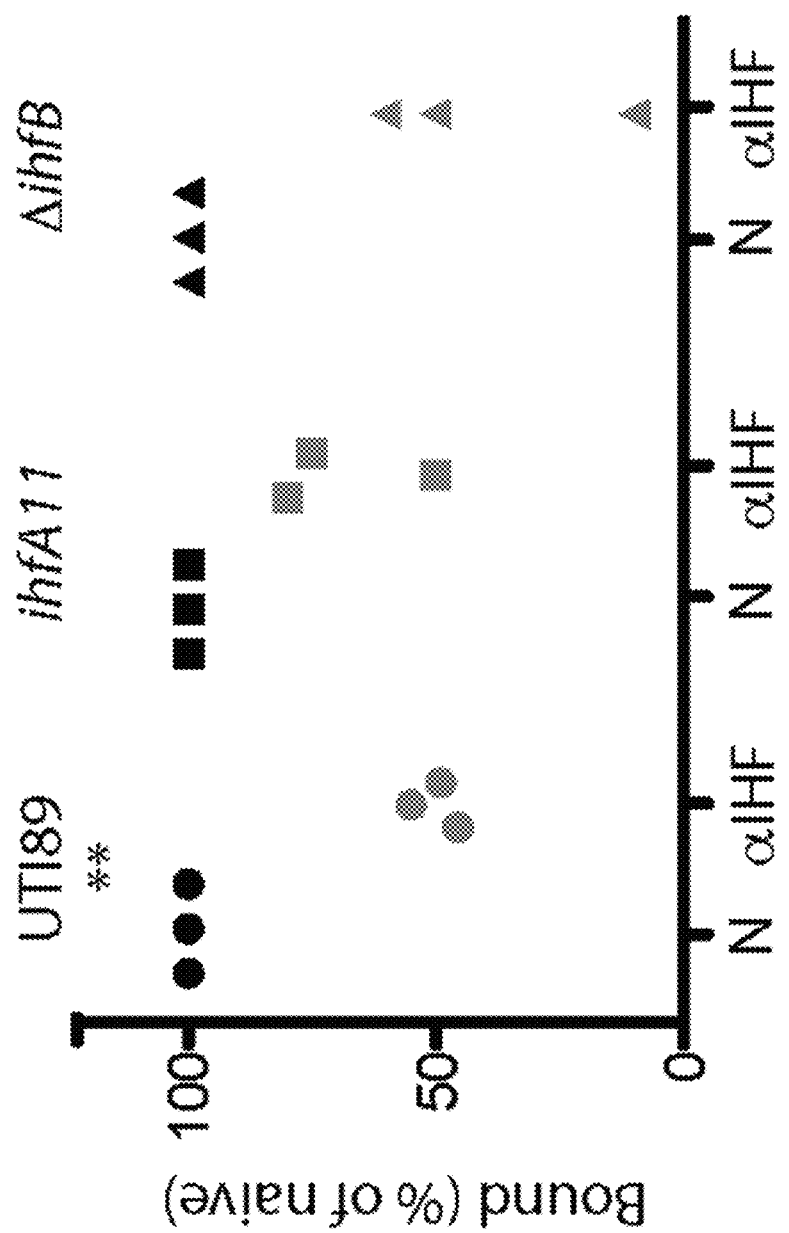
FIG. 6 shows that antiserum against IhfAB reduces UPEC binding to cultured bladder epithelial cells. HTB-4 human bladder transitional carcinoma cell monolayers were infected with UTI89 (circles), ROL745 (UTI89 ihfA11; squares), or ROL603 (UTI89 ΔihfB; triangles) treated with naïve antiserum (N; black) or specific antiserum directed against IhfAB (aIHF; gray). Each symbol represents the average of three experiments performed on the same day. Each experiment was replicated on three separate occasions. The number of bacteria bound is reported as a percentage of the bacteria bound in the presence of naïve serum. Statistical significance was determined by two-tailed Mann-Whitney test (**, p=0.003).

Antibody Against DNABII Family of Proteins Reduces UPEC Binding to Bladder Epithelia It has been demonstrated that vaccination against the DNABII family of proteins, specifically IHF, hastened resolution of otitis media caused by non-typeable *H. influenzae* in a mammalian model of disease (Goodman, S. D. et al. (2011) Mucosal Immunol. 4:625-637). In addition, we demonstrated that the addition of antisera directed against the DNABII family member, IHF, disrupts the integrity of UPEC communities grown on glass surfaces (Goodman, S. D. et al. (2011) Mucosal Immunol. 4:625-637). However, the use of an antibody-mediated therapeutic/preventative would have limited access to the cytoplasm of the superficial bladder epithelial cell and, as such, would be ineffective in the dissolution of the IBC. Applicants' observation that eIHF remains associated with the bacteria that recently egressed from the superficial epithelial cell (FIG. 5) prompted investigation to determine the potential utility of targeting eIHF to prevent binding and the subsequent invasion of UPEC into bladder epithelial cells. Without being bound by theory, it was hypothesized that the steric hindrance imposed by antibody binding to eIHF would preclude UPEC attachment to cultured human bladder epithelial cells. UTI89, UTI89 ihfA11::Tn10, or UTI89 ΔihfB were exposed to antisera directed against IHFab prior to introduction to a monolayer of bladder epithelial cells. The presence of the antisera directed against IhfAB markedly reduced the attachment of all strains tested (FIG. 6). Thus, the use of IHF as an immunogen can have utility in the reduction of UPEC adhesion to the bladder epithelial surface. The observation that the antibody reduced attachment in strains deficient of either subunit suggests that the heterodimer is not required for extrabacterial localization of the subunits.

The contribution of IHF to UPEC pathogenesis is multifactorial including: regulation of adhesion production, intracellular growth, and proper architecture of intracellular communities. Recent studies have provided insight into the inability of currently available antibiotics to eradicate UPEC from the bladder (Blango, M. G. et al. (2010) Antimicrob. Agents Chemother. 54:1855-1863). There is significant interest in new approaches to the eradication and control of UTIs (reviewed in (Sivick, K. E. et al. (2010) Infect. Immun. 78:568-585)). We have demonstrated that antibody interactions with eIHF demonstrate promise to prevent attachment to bladder epithelial cells (FIG. 6), the first essential step for colonization of the urinary tract. We would hypothesize that, should vaccination lead to high titer production of antibodies in the urine, that the initial binding event could be at least significantly reduced upon introduction of bacteria into the urinary tract and could also be effective in the attenuation of acute infections. The use of IHF as a target may also be affective against other uropathogens since the antibody used in this study was shown to be effective in targeting extracellular IHF in a number of bacterial pathogens (Goodman, S. D. et al. (2011) Mucosal Immunol. 4:625-637). Based on our findings here, there is at least a sufficient reliance on eIHF such that a UPEC infection could be ameliorated or even completely prevented by proper targeting of the immune system either through active immunization or even passive transfer of IHF specific antisera. The latter maybe highly efficacious in preventing infections derived from long-term urinary tract catheterizations.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

TABLE 2

| Bacteria strain | Abbreviation | Protein name(s) | |
| --- | --- | --- | --- |
| *S. sobrinus* 6715 | Ss | 1310 | (HU) (partial) |
| *S. pyogenes* MGAS10270 | Spyog | Spy1239 | (HU) |
| *S. gordonii* Challis NCTC7868 | Sg | SGO_0701 | (HlpA) |
| *S. agalactiae* (Group B Strep)2603V/R | GBS | SAG_0505 | (Hup) |
| *S. mutans* UA159 | Sm | Smu_589 | (HU) |
| *S. pneumoniae* R6 | Spneu | spr1020 | (HU) |
| *S. gallolyticus* UCN34 (*S. bovis*) | Sgall | YP_003430069 | (HlpA) |
| *S. aureus* MW2 | Sa | MW1362 | (HU) |
| *S. epidermidis* RP62A | Se | SERP1041 | (Hup) |
| *E. coli* K12-MG1655 | Ec | b1712 | (HimA) |
| | | b0912 | (HimD) |
| *H. influenza* KW20 Rd | Hi | HI1221 | (HimA) |
| | | HI1313 | (HimD) |
| | | HI0430 | (HupA) |
| *Salmonella enteric* serovar typhi CT18 | Salm | Sty1771 | (HimA) |
| | | Sty0982 | (HimD) |
| *Aggregatibacter actinomycetemcomitans* D11S-1 | Aa | YP_003255965 | (IHFalpha) |
| | | YP_003256209 | (IhfB) |
| | | YP_003255304 | (HU) |
| *P. gingivalis* W83 | Pg | PG_0121 | (Hup-1) |
| | | PG_1258 | (Hup-2) |
| *N. gonorrhoeae* FA1090 (Oklahoma) | Ng | NGO603 | (IHFβ) |
| | | NGO030 | (IHFα) |
| *N. meningitides* MC58 | Nm | NMB_0729 | (HimA) |
| | | NMB_1302 | (HimA) |
| *P. aeruginosa* | Pa | PA3161 | (HimD) |
| | | PA1804 | (HupB) |
| | | PA2758 | (HimA) |
| *H. pylori* 26695 | Hp | Hp0835 | (Hup) |
| *B. burgdorferi* B31 | Bb | BB_0232 | (Hbb) |
| *Moraxella catarrhalis* | Mc | | |
| *V. cholera* El Tor N16961 | Vc | VC_0273 | (HupA) |
| | | VC_1914 | (HipB) |
| | | VC_1919 | (HupB) |
| | | VC_1222 | (HimA) |
| *Burkholderia cenocepacia* HI2424 | Bc | Bcen2424_1048 | (IHFB) |
| | | Bcen2424_1481 | (IHFA) |
| *Burkholderia pseudomallei* 668 | Bp | BURPS668_2881 | (IHFB) |
| | | BURPS668_1718 | (IHFA) |
| *Mycobacterium tuberculosis* CDC1551 | Mtb | MT_3064 | (HU) |
| *Mycobacterium smegmatis* MC2 | Ms | MSMEG_2389 | (Hup) |
| *Treponema denticola* ATCC 35405 | Td | TDE_1709 | (HU) |
| *Treponema palladum* Nichols | Tp | TP_0251 | (DNA binding protein II) |
| *Prevotella melaninogenica* ATCC 25845 | Pm | PREME0022_2103 | (HupB) |
| | | PREME0022_0268 | (HupA) |
| | | PREME0022_0341 | (Hup) |
| | | PREME0022_0340 | (HimA) |
| *Prevotella intermedia* 17 | Pi | PIN_A0704 | (Hup) |
| | | PIN_A1504 | (Hup-2) |
| | | PIN_0345 | (HimA) |
| | | PIN_0343 | (Hypothetical protein) |
| *Bordetella pertusis* Tohama 1 | Bpert | BP2572 | (IhfA) |
| | | BP3530 | (HupB) |
| | | BP0951 | (IhfB) |

What is claimed is:

1. A method to inhibit or prevent infection of a cell by a bacteria that exports a DNABII protein, comprising administering to a tissue comprising the cell an antibody that specifically recognizes and binds the DNABII protein or an antibody fragment that specifically recognizes and binds the DNABII protein, in an amount effective to inhibit or prevent infection of the cell by the bacteria that exports the DNABII protein.

2. The method of claim 1, further comprising administering an effective amount of an additional antibacterial agent that is not the antibody that inhibits the growth of the bacteria or infection by the bacteria.

3. The method of claim 2, wherein the antibacterial agent is an antibiotic.

4. The method of any one of claim 1, 2, or 3, wherein the administering is in vitro or in vivo.

5. A method to treat a bacterial infection in a subject in need thereof, wherein the bacteria causing the infection exports a DNABII protein and wherein the subject is infected with the bacteria, the method comprising administering to the subject an antibody that specifically recognizes and binds the DNABII protein or an antibody fragment that specifically recognizes and binds the DNABII protein, in an amount effective to treat the bacterial infection in the subject.

6. The method of any one of claim 1 or 5, wherein the effective amount of antibody or an antibody fragment that specifically recognizes and binds the DNABII protein, is delivered in a microsphere or by coating an in situ device with the antibody an antibody fragment that specifically recognizes and binds the DNABII protein.

7. The method of claim 6, wherein the device is a catheter.

8. The method of claim 1, wherein the antibody is one or more of a polyclonal antibody, a monoclonal antibody, a humanized antibody, a human antibody, a veneered antibody, a diabody, a recombinant human antibody, or a chimeric antibody.

9. The method of claim 1, wherein the antibody is a polyclonal antibody.

10. The method of claim 1, wherein the antibody is a monoclonal antibody.

11. The method of claim 5, wherein the antibody is one or more of a polyclonal antibody, a monoclonal antibody, a humanized antibody, a human antibody, a veneered antibody, a diabody, a recombinant human antibody, or a chimeric antibody.

12. The method of claim 5, wherein the antibody is a polyclonal antibody.

13. The method of claim 5, wherein the antibody is a monoclonal antibody.

14. The method of claim 1, wherein the method comprises administering an effective amount of an antibody fragment that specifically recognizes and binds the DNABII protein.

15. The method of claim 5, wherein the method comprises administering an effective amount of an antibody fragment that specifically recognizes and binds the DNABII protein.

16. The method of claim 1, wherein the bacteria is selected from the group of *Vibrio vulnificus, Vibrio cholera, E. coli, Legionella pneumophila, Salmonella, Shigella, Listeria, Aggregatibacter, Neisseria, S. sobrinus, S. pyogenes, S. gordonii, S. agalactiae, S. mutans, S. pneumoniae, S. gallolyticus, S. aureus, S. epidermidis, H. influenzae, Salmonella enteric serovar typhi, Aggregatibacter actinomycetemcomitans, P. gingivalis, N. gonorrhoeae, N. meningitides, P. aeruginosa, H. pylori, B. burgdorferi, Moraxella catarrhalis, Burkholderia cenocepacia, Burkholderia pseudomallei, Mycobacterium tuberculosis, Mycobacterium smegmatis, Treponema denticola, Treponema palladum, Prevotella melaninogenica, Prevotella intermedia*, and *Bordetella pertussis*.

17. The method of claim 5, wherein the bacteria is selected from the group of *Vibrio vulnificus, Vibrio cholera, E. coli, Legionella pneumophila, Salmonella, Shigella, Listeria, Aggregatibacter, Neisseria, S. sobrinus, S. pyogenes, S. gordonii, S. agalactiae, S. mutans, S. pneumoniae, S. gallolyticus, S. aureus, S. epidermidis, H. influenzae, Salmonella enteric serovar typhi, Aggregatibacter actinomycetemcomitans, P. gingivalis, N. gonorrhoeae, N. meningitides, P. aeruginosa, H. pylori, B. burgdorferi, Moraxella catarrhalis, Burkholderia cenocepacia, Burkholderia pseudomallei, Mycobacterium tuberculosis, Mycobacterium smegmatis, Treponema denticola, Treponema palladum, Prevotella melaninogenica, Prevotella intermedia*, and *Bordetella pertussis*.

18. The method of claim 1 or 5, wherein the DNABII protein is a histone-like (HU) protein or an integration host factor (IHF) protein.

* * * * *

(12) EX PARTE REEXAMINATION CERTIFICATE (11867th)
United States Patent
Goodman et al.

(10) Number: US 9,745,366 C1
(45) Certificate Issued: Jun. 24, 2021

(54) COMPOSITIONS AND METHODS FOR THE PREVENTION OF MICROBIAL INFECTIONS

(71) Applicants: University of Southern California, Los Angeles, CA (US); Research Institute at Nationwide Children's Hospital, Columbus, OH (US)

(72) Inventors: Steven D. Goodman, Hilliard, OH (US); Sheryl S. Justice, Westerville, OH (US)

(73) Assignee: RESEARCH INSTITUTE AT NATIONWIDE CHILDREN'S HOSPITAL, Columbus, OH (US)

Reexamination Request:
No. 90/014,586, Oct. 5, 2020

Reexamination Certificate for:
Patent No.: 9,745,366
Issued: Aug. 29, 2017
Appl. No.: 14/493,051
Filed: Sep. 22, 2014

Related U.S. Application Data

(60) Provisional application No. 61/881,317, filed on Sep. 23, 2013.

(51) Int. Cl.
*A61K 39/395* (2006.01)
*C12Q 1/18* (2006.01)
*A61K 49/00* (2006.01)
*A61K 39/40* (2006.01)
*C07K 16/12* (2006.01)

(52) U.S. Cl.
CPC ............. *C07K 16/12* (2013.01); *C12Q 1/18* (2013.01); *C07K 2317/76* (2013.01); *G01N 2500/04* (2013.01); *G01N 2500/10* (2013.01)

(58) Field of Classification Search
None
See application file for complete search history.

(56) References Cited

To view the complete listing of prior art documents cited during the proceeding for Reexamination Control Number 90/014,586, please refer to the USPTO's public Patent Application Information Retrieval (PAIR) system under the Display References tab.

*Primary Examiner* — Bruce R Campell

(57) ABSTRACT

This disclosure provides methods and compositions to inhibit or prevent infection of a cell by a bacteria that exports DNABII proteins by administering to a tissue infected with the bacteria an effective amount of an antibody that specifically recognizes and binds the DNABII proteins, thereby inhibiting or preventing infection of the bacteria. Treatment methods, screens and kits are further provided.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-18 are cancelled.

\* \* \* \* \*

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 1

Trp Ala Thr Cys Ala Ala Asn Asn Asn Asn Thr Thr Arg
1               5                   10